(12) United States Patent
Gunderson et al.

(10) Patent No.: US 11,654,413 B2
(45) Date of Patent: May 23, 2023

(54) SYSTEM AND METHOD FOR ENHANCING EFFECTIVENESS OF PRODUCTS GENERATED FROM IONIZATION, OXIDATION, PHOTOOXIDATION, PHOTOCATALYTIC, AND PHOTOCHEMICAL REACTIONS

(71) Applicant: BIS SCIENCE LLC., Fort Worth, TX (US)

(72) Inventors: Marc W. Gunderson, Fort Worth, TX (US); Paul Dabney, Georgetown, TX (US)

(73) Assignee: BIS SCIENCE LLC., Fort Worth, TX (US)

( * ) Notice: Subject to any disclaimer, the term of this patent is extended or adjusted under 35 U.S.C. 154(b) by 0 days.

(21) Appl. No.: 17/829,742

(22) Filed: Jun. 1, 2022

(65) Prior Publication Data
US 2023/0076005 A1    Mar. 9, 2023

Related U.S. Application Data

(60) Provisional application No. 63/233,393, filed on Aug. 16, 2021.

(51) Int. Cl.
| | |
|---|---|
| *B01J 19/12* | (2006.01) |
| *A61L 2/26* | (2006.01) |
| *A61L 2/22* | (2006.01) |
| *C01B 13/10* | (2006.01) |
| *B01J 19/00* | (2006.01) |
| *A61L 101/02* | (2006.01) |

(52) U.S. Cl.
CPC ............... *B01J 19/123* (2013.01); *A61L 2/22* (2013.01); *A61L 2/26* (2013.01); *B01J 19/0006* (2013.01); *C01B 13/10* (2013.01); *A61L 2101/02* (2020.08); *A61L 2202/11* (2013.01); *A61L 2202/14* (2013.01); *A61L 2202/15* (2013.01); *B01J 2219/0801* (2013.01); *B01J 2219/1203* (2013.01)

(58) Field of Classification Search
CPC .......... A61L 2/22; A61L 2/26; A61L 2202/11; A61L 2202/14; B01J 19/123
See application file for complete search history.

(56) References Cited

U.S. PATENT DOCUMENTS

| | | | |
|---|---|---|---|
| 2006/0104858 A1* | 5/2006 | Potember | A61L 9/205 422/123 |
| 2015/0374867 A1* | 12/2015 | Patterson, Jr. | A61L 2/202 422/186.3 |
| 2019/0091360 A1* | 3/2019 | Markesbery | A01N 59/00 |

* cited by examiner

*Primary Examiner* — Sean E Conley

(74) *Attorney, Agent, or Firm* — Maier & Maier, PLLC

(57) ABSTRACT

Methods, systems, and apparatuses for producing one or more of trioxygen, hydrogen and its ions, oxygen and its ions, hydrons, hydroperoxyls, and electronically modified oxygen derivatives from oxidizing agents that are exposed to photon emissions at a wavelength in a range of 0.01 nm to 845 nm, wherein wavelengths that photo-dissociate trioxygen may be excluded. The methods, systems and apparatuses enhance the effectiveness of photo-oxidation, photocatalytic, and/or photochemical combined with photocatalytic reactions.

25 Claims, 2 Drawing Sheets

Week 4

| Test Microorganism | Contact Time | Test Substance | Replicate | CFU/Carrier | Average Percent Reduction Compared to Controls | Average Log₁₀ Reduction Compared to Controls |
|---|---|---|---|---|---|---|
| E. coli ATCC 11229 | Pre-Treatment | Numbers Control | 1 | 3.90E+04 | N/A | N/A |
| | 10 Minutes | Control Substance | 1 | 3.00E+04 | 23.08% | 0.11 |
| | | Sample 1 | 1 | 6.00E+03 | 84.62% | 0.81 |
| | | Sample 2a | 1 | 9.00E+03 | 76.92% | 0.64 |

FIGURE 2

SYSTEM AND METHOD FOR ENHANCING EFFECTIVENESS OF PRODUCTS GENERATED FROM IONIZATION, OXIDATION, PHOTOOXIDATION, PHOTOCATALYTIC, AND PHOTOCHEMICAL REACTIONS

CROSS-REFERENCE TO RELATED APPLICATIONS

This application claims priority to U.S. Provisional Patent Application No. 63/233,393, filed Aug. 16, 2021, the entire contents of which are incorporated herein by reference.

BACKGROUND

The photon is a type of elementary particle. It is the quantum of the electromagnetic field including electromagnetic radiation such as light and radio waves, and the force carrier for electromagnetic force. A photon is the smallest discrete amount or quantum of electromagnetic radiation. It is the basic unit of all light. Photons are massless, so they always move at the speed of light in vacuum, 299,792,458 m/s (or about 186,282 mi/s). Like all elementary particles, photons are currently best explained by quantum mechanics and exhibit wave-particle duality, their behavior featuring properties of both waves and particles.

Biophotons are photons of light in the ultraviolet and low visible light range that are produced or utilized by a biological system. They are non-thermal in origin, and the emission of biophotons is technically a type of bioluminescence, though bioluminescence is generally reserved for higher luminance luciferin/luciferase systems.

When a photon gets to a material, it is reflected, scattered, and/or absorbed by the material. The material then sets up an internal electromagnetic vibration that is not precisely a "photon"—it's called a "phonon". The phonon has a less-than-light velocity that depends on the properties of the material. A phonon is a definite discrete unit or quantum of vibrational mechanical energy, just as a photon is a quantum of electromagnetic or light energy. At each frequency, quantum mechanics principles dictate that the vibrational energy must be a multiple of a basic amount of energy, called a quantum, that is proportional to the frequency. Physicists call these basic levels of energy phonons. In a sense, "phonon" is a word to represent a particle of heat.

There are two main types of atomic motion in a liquid: phonon motion and diffusional motion due to an atom jumping between two equilibrium positions. In turn, phonon motion and diffusional motion include kinetic and potential parts, giving the liquid energy as $$E = K_l + P_l + K_s(\omega > \omega_F) + P_s(\omega > \omega_F) + K_d + P_d \quad (1)$$

where $K_l$ and $P_l$ are kinetic and potential components of the longitudinal phonon energy, $K_s(\omega > \omega_F)$ and $P_s(\omega > \omega_F)$ are kinetic and potential components of the energy of shear phonons with frequency $\omega > \omega_F$, and $K_d$ and $P_d$ are kinetic and potential energy of diffusing atoms. Diffusion is the net movement of anything (for example, atoms, ions, molecules, energy) from a region of higher concentration to a region of lower concentration. Diffusion is driven by a gradient-variation in concentration. So, phonon motion (heat motion) and diffusional motion work together so that temperature and composition are the same throughout a liquid.

In practice, most materials are filled with an ever-changing mix of phonons that have different frequencies and are traveling in different directions, all superimposed on each other, in the same way that the seemingly chaotic movements of a choppy sea can (theoretically) be untangled to reveal a variety of superimposed waveforms of different frequencies and directions. But unlike photons, which generally don't interact if they have different wavelengths, phonons of different wavelengths can interact and mix when they bump into each other, producing a correspondingly different wavelength. This makes their behavior much more chaotic and thus difficult to predict and control.

Oxidation is the loss of electrons during a reaction by a molecule, atom or ion.

Oxidation occurs when the oxidation state of a molecule, atom or ion is increased. The opposite process is called reduction, which occurs when there is a gain of electrons or the oxidation state of an atom, molecule, or ion decreases.

Photoexcitation is the production of an excited state of a quantum system by photon absorption in a targeted material or substance. The excited state originates from the interaction between a photon and/or phonon and the quantum system. On the atomic and molecular scale, photoexcitation is the photoelectrochemical process of electron excitation by photon absorption when the energy of the photon is too low to cause photoionization.

Multi-photon absorption (MPA) or multi-photon excitation or non-linear absorption is the simultaneous absorption of two or more photons of identical or different frequencies to excite a molecule from one state (usually the ground state) to a higher energy, most commonly an excited electronic state. MPA is one of a variety of multi-photon processes. In this specific process, two or more photons are absorbed by a targeted sample simultaneously. Neither photon may be at resonance with the available energy states of the system, however, the combined frequency of the photons is at resonance with an energy state. In quantum mechanics, an excited state of a system is any quantum state of the system that has a higher energy than the ground state (that is, more energy than the absolute minimum). Absorption of two or more photons with different frequencies is called "non-degenerate" MPA. Since MPA depends on the simultaneous absorption of two or more photons, the probability of MPA is proportional to the square of the photon intensity, thus it is a nonlinear optical process. The energy difference between the involved lower and upper states of the molecule is equal or smaller than the sum of the photon energies of the two or more photons absorbed. MPA is a third-order process, with absorption cross section typically several orders of magnitude smaller than one-photon absorption cross section.

Ionization is the process by which an atom or a molecule acquires a negative or positive charge by gaining or losing electrons, often in conjunction with other chemical changes. Ionization energy, also called ionization potential, in chemistry and physics, is the amount of energy required to remove an electron from an isolated atom or molecule. There is an ionization energy for each successive electron removed.

SUMMARY

The present disclosure is directed to methods for enhancing the effectiveness of products generated from ionization, oxidation, photo-oxidation reactions, photocatalytic reactions, photochemical reactions, and/or photochemical combined with photocatalytic reactions. Various embodiments of the reactions contain one or more, hydrogen and/or its isotopes, oxygen and/or its isotopes, electronically modified oxygen derivatives, reactive oxygen species, trioxygen, and free radicals. Various embodiments of the methods include steps of applying at least one oxidizing agent to a target or a substance to be treated, applying photon and/or phonon emissions at one or more wavelength in a range from 0.01 nm through 845 nm to the oxidizing agent, the target, and/or the substance to be treated, wherein wavelengths that photo-dissociate trioxygen are may be excluded, and performing an oxidizing reaction between the at least one oxidizing agent and the target and/or substance to be treated, which produces the photo-oxidation reaction products, photocatalytic reaction products, photochemical reaction products, and/or photochemical combined with photocatalytic reaction products, wherein the photo oxidation reaction products, photocatalytic reaction products, photochemical reaction products, and/or photochemical combined with photocatalytic reaction products generate at least one of trioxygen, hydrogen and its ions, oxygen and its ions, hydrons, hydroperoxyls, hydroxyl radical, and electronically modified oxygen derivatives. The wavelength range of 0.01 nm through 845 nm represents the lower level of x ray radiation at 0.01 nm to the upper level of 845 nm which is the upper border of the wavelengths that dissociate water. Multi-photon absorption (MPA) is a third order nonlinear optical phenomenon in which a molecule absorbs multiple photons at the same time. The transition energy for this process is equal to the sum of the energies of the multiple photons absorbed. In this disclosure, ionizing radiation in the form of a photon is a quantum of electromagnetic radiation. Its energy is given by $E=hf$ and is related to the frequency f and wavelength $\lambda$ of the radiation by $E=hf=hc\lambda$ (energy of a photon) where E is the energy of a single photon and c is the speed of light. When working with small systems, energy in eV is often useful. Note that Planck's constant in these units is $h=4.14\times10-15$ eV·s. Since many wavelengths are stated in nanometers (nm), it is also useful to know that $hc=1240$ eV·nm. Photons act as individual quanta and interact with individual electrons, atoms, molecules, and so on. The energy a photon carries is, thus, crucial to the effects it has. As stated above, the transition energy is equal to the sum of the energies of the multiple photons. This fact is often overlooked when discussing photons and ionization energy. Multiple photons that individually do not possess sufficient energy to ionize a substance may in fact create an ionization reaction through MPA.

The present disclosure is also directed to systems configured to perform a method for enhancing the effectiveness of products generated from photo-oxidation reactions, photocatalytic reactions, photochemical reactions, and/or photochemical combined with photocatalytic reactions. Various embodiments of the system are configured to perform embodiments of the methods disclosed herein. Various embodiments of the system include a reaction area, in which at least one oxidizing agent functions together with photon and/or phonon emissions to perform an oxidation reaction so that products of the oxidation reaction can be collected and/or separated at any time during the reaction, at least one oxidizing agent introducing component for applying the at least one oxidizing agent to the target and/or substance to be treated, and at least one photon emitting component for creating the photon emissions. In some embodiments of this disclosure, the reaction area could be an area such as a structure, room or building. In other embodiments, the reaction area could be a container or multiple containers. The reaction area utilized throughout this disclosure is where the various described reactions may or will take place. The reactions of this disclosure may produce a precipitate. If the produced precipitate is wanted separately from the other reactants, it may be collected by any suitable means such as centrifugation, filtering or any other suitable means. To apply the oxidizing agent to an area or target where the described reaction or reactions are to take place, any suitable method may be utilized. These oxidizing agent introducing components may include devices that mist, spray, fog, pour, flow or any other desired means of introducing the oxidizing agent to the target or area to be treated. Before, during and/or after the oxidizing agent is applied to the target or area, the oxidizing agent may be exposed to photons by a photon emitting component. Any desired photon emitting component may be used such as a: x-ray generator, a bulb, a LED, natural light or any other source of photons that have wavelengths from 0.01 nm through 845 nm.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the embodiments, and the embodiments include all such substitutions, modifications, additions, or rearrangements.

BRIEF DESCRIPTION OF THE DRAWINGS

Non-limiting and non-exhaustive embodiments of the disclosure are described with reference to the following figures and detailed description.

FIG. 2 illustrates enhanced effectiveness produced by an embodiment of the reaction, according to the present disclosure.

DETAILED DESCRIPTION

Figure 1:
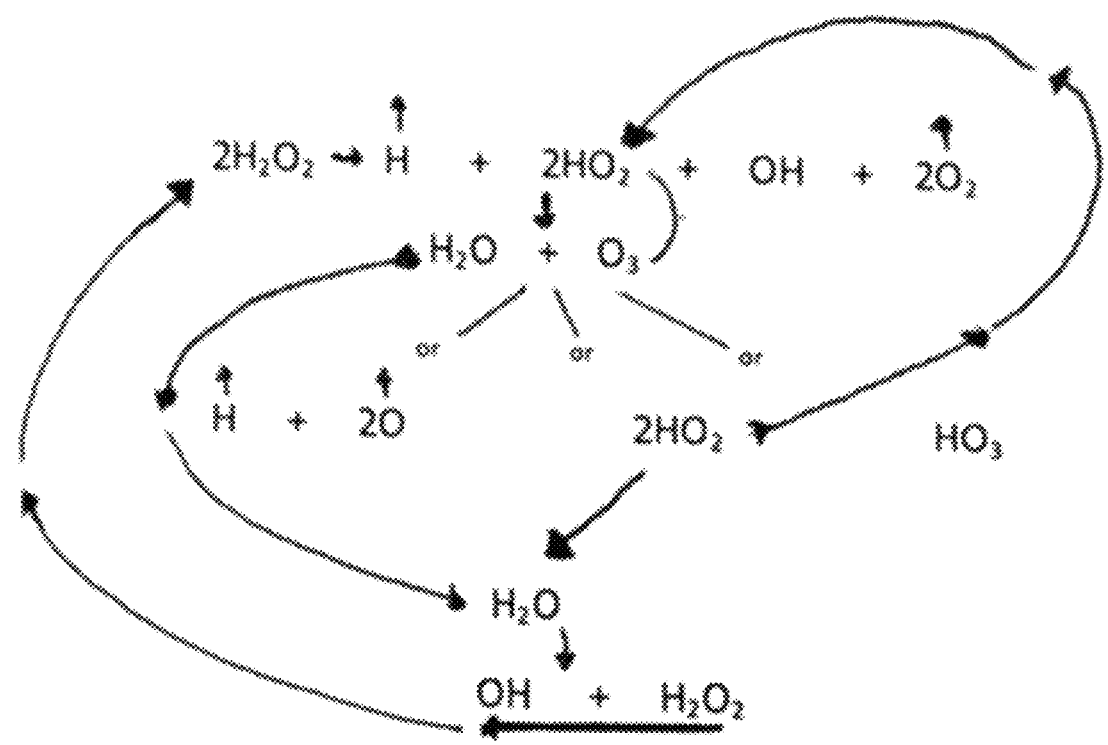
FIG. 1 is an exemplary diagram showing that a reaction can occur from a reactant molecule via an intermediate such as hydroperoxyl to form a trioxygen molecule, according to embodiments of the present disclosure.

Aspects of the present disclosure are disclosed in the following description and related drawings directed to specific embodiments. Alternate embodiments may be devised without departing from the spirit or the scope of the disclosure. Additionally, well-known elements of exemplary embodiments will not be described in detail or will be omitted so as not to obscure the relevant details of the disclosure.

As used herein, the word "exemplary" means "serving as an example, instance, or illustration." The embodiments described herein are not limiting, but rather are exemplary only. The described embodiments are not necessarily to be construed as preferred or advantageous over other embodiments. Moreover, the terms "embodiment or "embodiments" do not require that all embodiments of the disclosure include the discussed feature, advantage, or mode of operation.

In the methods and systems disclosed herein, methods of utilizing both homogeneous and heterogeneous photocatalytic (PCA) reactions are described. By utilizing both types of PCA, a photon/phonon enhanced self-sustaining reaction is produced resulting in electronically modified oxygen derivatives that are continuously produced as long as reactants are present. Trioxygen is one of the potential photocatalysts. This self-sustaining reaction results in an increased efficacy and a shelf life of increased and sustainable reactivity.

As used herein, the terms "and/or" and "and or" as used herein means that two or more elements are to be taken together or individually. Thus, "A and/or B" and "A and or B" cover embodiments having element A alone, element B alone, or elements A and B taken together.

Water absorbs UV radiation near 125 nm, exiting the 3a1 orbit and leading to dissociation into OH⁻ and H⁺. Through MPA, this dissociation can also be achieved by two or more photons at other nm wavelengths. This creates reactions and products, and embodiments of the present disclosure, that have not been previously reported or understood. Multiphoton absorption and two photon absorption (TPA) are terms used to describe a process in which an atom or molecule makes a single transition between two of its allowed energy levels by absorbing the energy from more than a single photon.

Chemi-excitation via oxidative stress by reactive oxygen species (ROS), and/or catalysis by enzymes is a common event in biomolecular systems. The present disclosure relates to utilizing photons and/or phonons in a synergistic chemi-excitation process that generates ROS, hydrogen and its isotopes, oxygen and its isotopes, water and its isotopes, hydrons, hydroperoxyls, and electronically modified oxygen derivatives (EMODs). According to various embodiments of the present disclosure, such reactions lead to the formation of triplet excited species such as trioxygen (ozone, $O_3$), trioxidane and others. This process contributes to spontaneous biophoton emission and indicates that biophoton emission can be increased by depleting assayed tissue of antioxidants or by addition of carbonyl derivatizing agents. In further embodiments, photon emission is increased by addition of EMODs such as hydroxyl radicals, hydroperoxides, hydrogen polyoxides, singlet oxygen, hydrogen, superoxide, and others.

Electromagnetic radiation moves in vacuum at a universal speed. This is the speed of light, c=30,000,000,000 centimeters per second (usually written in powers of ten, $c=3 \times 10^{10}$ cm/sec). The constant value of the speed of light in vacuum goes against our intuition: we would expect that high energy (short wavelength) radiation would move faster than low energy (long wavelength) radiation. We can consider light as a stream of tiny packets of energy, photons and biophotons and generating phonons, which creates a pulsating electromagnetic disturbance. A single photon or biophoton differs from another photon or biophoton only by its energy. In empty space (vacuum), all photons and biophotons travel with the same speed or velocity.

Photons and biophotons are slowed down, generating phonons, when they interact with different media such as water, glass or even air. This slowing down accounts for the refraction or bending of light. Refraction is the bending of a wave when it enters a medium where its speed is different. The refraction of the photon when it passes from a fast medium to a slow medium bends the photon toward the normal to the boundary between the two media. The amount of bending depends on the indices of refraction of the two media and is described quantitatively by Snell's Law. As the speed of the photon is reduced in the slower medium, the wavelength is shortened proportionately. The wavelength of the photon, phonon and biophotons is changed. This comes into play in certain embodiments of the present disclosure when wavelengths of dissociation are discussed. Different energy photons and biophotons are slowed by different amounts in glass or water or other substances; this leads to the dispersion of electromagnetic radiation and phonons. As used herein, greater intensity of light means that more photons are available to hit a target per second and more electrons could be ejected from a target, not that there was more energy per photon or biophoton.

The energy of the outgoing electrons depends on the frequency of photons used. There are two main kinds of interactions through which photons deposit their energy—both are with electrons. In one type of interaction the photon loses all its energy; in the other, it loses a portion of its energy, and the remaining energy is scattered—generating phonons and/or more photons. The energy € of the incoming photons and biophotons is directly proportional to the frequency, which can be written as E=hf in which h is a constant. Max Planck first proposed this relationship between energy and frequency in 1900 as part of his study of the way in which heated solids emit radiation. In one example, the photoelectric (photon-electron) interaction, a photon transfers all its energy to an electron located in one of the atomic shells. The electron is ejected from the atom by this energy and begins to pass through the surrounding matter. The electron rapidly loses its energy and moves only a relatively short distance from its original location. The photon's energy is deposited in the matter close to the site of the photoelectric interaction. The energy transfer is a two-step process. The photoelectric interaction in which the photon transfers its energy to the electron is the first step. The depositing of the energy in the surrounding matter by the electron is the second step. Phonons and electrons are the two main types of elementary particles or excitations generated with photon reactions.

If the binding energy is more than the energy of the photon, a photoelectric interaction that results in the feeing of an electron cannot occur. This interaction is possible only when the photon has sufficient energy to overcome the binding energy and remove the electron from the atom or a MPA reaction can occur depositing sufficient energy. The photon's energy is divided into two parts by the interaction. A portion of the energy is used to overcome the electron's binding energy and to remove it from the atom. The remaining energy is transferred to the electron as kinetic energy (phonon) and is deposited near the interaction site. Since the interaction creates a vacancy in one of the electron shells, typically the K or L, an electron moves down to fill in. The drop in energy of the filling electron often produces a characteristic x-ray photon, endogenous x-ray radiation. The energy of the characteristic radiation depends on the binding energy of the electrons involved. Characteristic radiation initiated by an incoming photon is referred to as fluorescent radiation. Fluorescence, in general, is a process in which some of the energy of a photon is used to create a second photon of less energy. This process sometimes converts x-rays into light photons. Whether the fluorescent radiation is in the form of light or x-rays depends on the binding energy levels in the absorbing material.

As defined herein, the linear attenuation coefficient (μ) is the actual fraction of photons interacting per 1-unit thickness of material. Linear attenuation coefficient values indicate the rate at which photons interact as they move through material and are inversely related to the average distance photons travel before interacting. The rate at which photons interact (attenuation coefficient value) is determined by the energy of the individual photons or the MPAs, and the atomic number and density of the material. This is important to the activation of the enhanced antimicrobial oxidizing agent according to various embodiments of the disclosure. In some situations, it is more desirable to express the attenuation rate in terms of the mass of the material encountered by the photons and or phonons rather than in terms of distance. The quantity that affects attenuation rate is not the total mass of an object but rather the area mass. Area mass is the amount of material behind a 1-unit surface area, and is the product of material thickness and density:

Area Mass(g/cm$^2$)=Thickness(cm)×Density(g/cm$^3$).

The mass attenuation coefficient, using this formula, is the rate of photon and or phonon interactions per 1-unit (g/cm$^2$) area mass. According to various embodiments of the disclosure, by establishing a linear attenuation coefficient that does not diminish too rapidly with the functioning distance so that sufficient numbers of photons and or phonons are available for enhancement of the oxidizing agent, an effective enhanced antimicrobial, enhanced catalyst, enhanced bleaching agent, or enhanced other effects of reactive oxygen species and oxidizing agent are generated. In various embodiments, the enhanced antimicrobial, catalyst, bleaching agent, reaction potential or other effects are used in the disclosed process in plasma, liquid, gas, solid, or a combination of these states of matter. It is also displayed in various embodiments of the agglomeration process disclosed herein.

Brownian diffusion is the characteristic random wiggling motion of small particles, resulting from constant bombardment by surrounding molecules. Such irregular motions of pollen grains in water were first observed by the botanist Robert Brown in 1827, and later similar phenomena were found for small smoke particles in air. In agglomeration, suspended particles tend to adhere one to the other creating bigger and heavier aggregates. The agglomeration process includes the transportation and collision of particles, and the attachment of the particles to other particles. Understanding particle agglomeration and aggregation and the mechanisms that cause such assemblies, such as diffusion, is important in a wide range of processes and applications described in this disclosure.

As used herein, aggregation and agglomeration are two terms that are used to describe the assemblage of particles in a sample but clustering via agglomeration is irreversible. The main transport mechanisms by which particles can collide are Brownian motion, laminar or turbulent flow, or relative particle settling and gravitational agglomeration. In various embodiments of the disclosure, gravitational agglomeration, which is dependent on the size of the particles and their terminal velocity, is one component relating to the separation of particles in air, solutions or associated with a compound or material. Slowly settling particles interact with the more rapidly settling particles, leading to the formation of clusters of precipitate particles. This process can be called agglomeration. Several different basic effects have been studied as being responsible for particle collision and agglomeration, which are mainly orthokinetic and hydrodynamic forces. In the case of orthokinetic collisions, the effective agglomeration rate constant or agglomeration input can be described as a product of the collision rate constant ($\beta_{coll}$) and an efficiency factor $\psi$.

$$\beta=\psi\beta_{coll}$$

$\beta_{coll}$ increases linearly with the shear rate. Whereas the efficiency factor w decreases strongly in a high shear region. Although $\beta$ should be size-dependent, experimental agglomeration data can often be fitted with a size-independent input. It has been shown that $\beta_{coll}$ has a dependence on the mean particle size. The efficiency factor includes the supersaturation dependence that is needed for the cementation of the particles. Brownian diffusion is instrumental in particle size selection for diffusion of photon/phonon enhanced oxidizing agent solutions dispersed in a fog, mist, vapor, spray, bolus, drop, stream, or other methods of dispersion.

Rates of reaction are based on collision theory. Increasing the number of collisions can lead to faster reaction rate. Increasing the concentration causes more collisions and so a faster reaction rate. Temperature increases the speed of the particles so more collisions and a faster reaction rate. Size of particles has an effect on solubility reactions so smaller pieces or smaller droplets have greater surface areas relative to the volume. A decrease in particle size causes an increase in the substance's total surface area when concentration remains unchanged.

Liquids evaporate only from the surface of a droplet. If the surface area of the droplet in relation to the volume is decreased, then the evaporation efficiency is increased. A substance existing in a liquid phase can be transferred to a gaseous phase by utilizing and controlling droplet size. The time needed for this phase transfer can be regulated by selecting the proper sized droplet.

TABLE 1

| FOG CLASSIFICATION | DROPLET SIZE In microns | TIME FOR PARTICLE TO FALL 10 FEET (SECONDS) |
|---|---|---|
| Wet Fog | 11-49 | 40-1,020 |
| Dry Fog | 6-10 | 1,019-12,000 |
| Extreme Dry Fog | 2-4 | 12,001-25,400 |
| Sub 2 Micron Dry Fog | <2 | >25,400 |

As shown in Table 1, the smaller the droplet size, the longer it can stay air borne. Therefore, the smaller the droplet size the faster and more efficient evaporation is achieved. According to various embodiments of this disclosure, the various micron-sized droplets created by the systems described in the present disclosure evaporate at selected rates depending on application needs. In some embodiments, small size particles are selected, and they are sized so that they completely evaporate into the air before reaching most surfaces. This near 100% evaporation rate achieves near 100% chemical efficiency. In some embodiments, the particle fall rate is calculated based on density, size, and mass of the particle as well as the density of the air or gas it is placed in. Humidity also influences the fall rate outcome because at a low humidity a particle will tend to evaporate faster and lose size and mass as it remains air borne. These factors enable various embodiments of a selected size micron fog microbial suppression system, and/or agglomeration system, and/or bleaching system, or other applicable uses of this system to utilize an extremely low volume and low concentration of a photon/phonon enhanced oxidizing agent solution.

According to various embodiments, the photon/phonon enhanced oxidizing agent solution is deposited into a volume of liquid, plasma, air, or gas, or other suitable medium. In various embodiments, this is done through an existing HVAC system, a fogging device, a sprayer, a mister, an injector, a dropper, a spray can, an aerial spraying device, crop dusting, or other suitable devices. Various embodiments of the photon/phonon enhanced oxidizing agent system exhibit such a slow particle fall rate that when it is combined with the simultaneous phase change of these particles that a concentration of gas vapor (e.g., of air borne dispersion) is created and maintained of the photon/phonon enhanced oxidizing agent in the air.

The present disclosure is further directed to a system for progressive regression of Colony Forming Units (CFUs) from the continuous presence of a photon/phonon enhanced microbial suppression system. Embodiments of the system provide a decontamination system that includes a photon/ phonon enhanced microbial suppression system solution and its effects on substances that it contacts. Various embodiments utilize a photon/phonon and MPA enhanced microbial suppression system that includes particle size considerations for controlled dispersion and addresses agglomeration of inactivated microbes and other precipitates in a multi-faceted technology described by this system. In various embodiments, this combination provides a means of decontaminating areas, structures, food, liquids, animals, animal fluids, plants, buildings, pipelines, homes, offices, indoors and outdoors. Some embodiments feature low chemical concentrations made effective with the combination of the photon/phonon enhanced oxidizing agent microbial suppression system, so that there are reduced or no harmful effects on humans or animals or plants when administered at low concentrations, and so exposure to the agents can be a singular event or on going, constant, or nearly constant.

According to various embodiments, other uses of the photon/phonon enhanced oxidizing agent system involve the dissociation of blood and other animal fluids. As a non-limiting example, blood cells contain a dramatic amount of potentially usable components such as proteins, fats, minerals, elements, and small molecular weight constituents that once separated allow disposal or repurposing of the resultant liquid in environmentally sound methods such as irrigation of crops. Animal fluids, blood, blood cells, microbes, and organic matter tend to be more difficult to dispose of as compared to serum or plasma. Blood, for example, tends to be less stable and contains total dissolved solids (TDS), total suspended solids (TSS), microbes and other components that complicate its disposal unless it is dissociated, decontaminated, and separated. This is one of the major reasons why, for example, blood plasma (often simply referred to as plasma, i.e., an anticoagulated whole blood sample; deprived of cells and erythrocytes) and blood serum (often simply referred to as serum, i.e., coagulated whole blood; deprived of cells, erythrocytes, and most proteins of the coagulation system, especially of fibrin/fibrinogen) are considered biohazards. Various embodiments of the present disclosure include a decontamination system whereby blood components go through the described agglomeration process whereby photon and/or phonon enhanced oxidizing agents are added to the blood causing dissociation of the blood into constituent components allowing for these components to be used for their water value and nutritional value and other desired purposes.

As used herein, organic matter pertains to any carbon-based compound that exists in nature. Living things are described as organic since they are composed of organic compounds. Examples of organic compounds are carbohydrates, lipids, proteins, and nucleic acids. Since they contain carbon-based compounds, they are broken down into smaller, simpler compounds through decomposition and through dissociation when exposed to oxidizing agents that have been subject to photon emissions from 0.01 nm through 845 nm. Living organisms also excrete or secrete material that is considered an organic material. The organic matter from blood contains useful substances that have value when separated from the blood. This organic matter contains substances that can be repurposed as food sources, as fertilizer, as medicines, or other uses. According to various embodiments, the decontaminated liquid that has had particles removed through agglomeration when exposed to oxidizing agents that have been exposed to photon emissions from 0.01 nm through 845 nm with the wavelengths that dissociate trioxygen excluded or reduced. These fluids may be used to irrigate land and/or for liquids for animals to ingest. In various embodiments, the photon, emissions are a single wavelength or exist as multiple wavelengths.

According to various embodiment, reactions described in the present disclosure provide a multitude of uses. In some embodiments, such as HVAC applications, a low concentration of 1 part per million (ppm) of an enhanced oxidizing agent or less is used. In other embodiments, a higher concentration of oxidizing agents of 50% or more are advantageous. In various embodiments, variables such as temperature, opacity of reactants, pH and others influence the selection of concentration of oxidizing agents. In some embodiments, an oxidizing agent is added to a substance (target) for antimicrobial purposes. In some embodiments, the effect of the photon/phonon emissions takes place at a certain time or place. In these embodiments, the photon emissions will not be applied to the oxidizing agent/target mixture until such time as the enhanced reaction is desired to take place. In other instances, the photon emissions are applied to the oxidizing agent before it is applied to the target. An example of this is an antimicrobial and agglomeration effect in a HVAC system where applying the photon/phonon emissions to the oxidizing agent before it is introduced to the ambient air is better to suited to use than applying the photon/phonon emissions to the entire volume of ambient air of the structure serviced by the HVAC system.

At present, appropriate separation/handling of animal fluids, blood, blood cells, microbes, and organic matter, e.g., by centrifugation, filtration, heating, cooling, precipitation, or analyte extraction is essential, before such processed sample can be properly and reliably disposed of or repurposed. As disclosed above, serum or plasma may be obtained from whole blood and repurposed as nutrients or fertilizer, or disposed of as needed. Cells, cell constituents, microbes, organic matter, and other components of animal fluids may also be removed by filtration and/or centrifugation from blood or blood components or from other animal fluids but a lower cost method is desired over present commercially available techniques. According to various embodiments of the present disclosure, in techniques of sample processing, the animal fluids, blood, blood cells, microbes, and other organic matter of interest are first separated from the majority of substances by dissociation, agglomeration, and/or extraction methods when exposed to oxidizing agents that have been exposed to photon emissions from 0.01 nm through 845 nm. In various embodiments, extraction is performed in liquid phase or in a solid phase. In various embodiments, gross extraction of larger particles is sequenced with extraction methods processing progressively smaller units until the desired resolution is obtained. Various embodiments of the present disclosure allow for this process to be accomplished by utilization of photon/phonon emissions and their activation of oxidizing agent solutions.

In various embodiments of the present disclosure, a photon/phonon emission activated antimicrobial oxidizing agent solution is applied to air via a HVAC system or other suitable means. In some embodiments, a small micron (less than 20 microns droplet size) mist or fog photon MPA enhanced microbial suppression system is selected to utilize an extremely low volume and low concentration of a photon/phonon enhanced antimicrobial oxidizing agent solution into a volume of air or gas. In various embodiments, a 6-10-micron droplet size, 2-4 micron droplet size, or a sub 2 micron droplet size mist or fog photon MPA enhanced microbial suppression system is selected.

According to various embodiments, this is done through an existing HVAC system utilizing an electrostatic fog, fogging, misting, spraying, sprinkling, diffuser, atomizer, or other suitable device. In some embodiments, the application device includes one or more of an aerosolizing nozzle or piezoelectric fogger producing a small micron dry fog, an air compressor to push the solution through the nozzle at the desired rate, a metering pump to dispense the solution at a rate that will give the desired concentration in ambient air, and a control system to regulate and monitor the application of the solution. In some embodiments, a small micron dry fog photon MPA enhanced oxidizing agent microbial suppression system exhibits such a slow particle fall rate that when it is combined with the simultaneous evaporation of these particles, a concentration of gas vapor is created and maintained of the photon enhanced antimicrobial agent in the HVAC serviced air. A progressive regression of CFUs from the continuous presence of the small micron dry fog microbial suppression system provides, in the ambient air, a decontamination system of air and surfaces that the small micron dry fog microbial suppression system solution contacts. In some embodiments, as the photon enhanced antimicrobial oxidizing agent settles through the ambient air, it inactivates microbes, and any remaining hydrogen peroxide in the ambient air decomposes into oxygen and water. In various embodiments, the small micron dry fog microbial suppression system is designed so that most of the microbial inactivation occurs in the HVAC system ducts and in the higher levels of a building's ambient air. By design, in various embodiment, the concentration of hydrogen peroxide becomes lower as it is consumed by inactivating microbes, by evaporation, and by decomposition into oxygen and water. This demonstrates another, very different application of the technology displayed in the present disclosure.

Oxidative biocides (such as chlorine and hydrogen peroxide ($H_2O_2$)) remove electrons from susceptible chemical groups, oxidizing them, and become themselves reduced in the process. Oxidizing agents are often low-molecular-weight compounds and are considered to pass easily through cell walls/membranes, whereupon they may react with internal cellular components, leading to apoptotic and necrotic cell death. Although the biochemical mechanisms of action may differ between oxidative biocides, the physiological actions are largely similar. Oxidative biocides have multiple targets within a cell as well as in almost every biomolecule; these include peroxidation and disruption of membrane layers, oxidation of oxygen scavengers and thiol groups, enzyme inhibition, oxidation of nucleosides, impaired energy production, disruption of protein synthesis and, ultimately, cell death.

According to various embodiments of the present disclosure, a generated photon MPA enhanced microbial suppression system acts like a filter in that a microbial particle cannot pass through it without colliding with a photon and or phonon enhanced antimicrobial particle. When a microbe collides with a photon and or phonon enhanced antimicrobial particle, agglomeration occurs. As agglomerized microbial particles bind together, their mass increases as a unit. Gravitational forces acting on the photon enhanced agglomerized microbial particles increase its velocity of fall. The photon enhanced agglomerized microbial particles continue to gather more microbial particles as it falls through the selected medium such as liquids, air, or a gas. An analogy would be a snowball rolling downhill continually increasing in size as it advances downhill. Since photon enhanced antimicrobial particles contain an enhanced oxidizing agent, the microbe that contacts the photon enhanced oxidizing agent becomes agglomerized as it comes in contact with the antimicrobial sanitizer/disinfectant, filter particles. These agglomerized particles settle or are filtered to remove them from the solution, air, gas, liquid, or plasma.

According to various embodiments, this phenomenon is called agglomeration and solving microbial problems with a photon MPA microbial suppression particle utilizes embodiments of agglomeration described in the present disclosure. As used herein, agglomeration is the gathering of particle mass into a larger mass, or cluster. While this is occurring, embodiments of the photon/phonon enhanced antimicrobial oxidizing agent is killing and/or deactivating the microbes. The agglomerated dead and/or deactivated microbe is pulled by gravitational forces and eventually settles from the substance being treated. In various embodiments, the substance is a liquid, gas, plasma, or any suitable substance selected to be treated. This agglomeration of dead or inactivated microbes and other substances such as proteins and minerals is unique for a variety of reasons. As an example, in conditioned air, it has been shown that even in common air filters, such as HEPA filters designed to filter out microorganisms, arrested microorganisms can grow and, in some cases, "grow through" the filter medium and seed the air with an ever-increasing dose of microbes. Some organic media such as cellulose media provide nutrition for microbiological growth.

Various embodiments of the present disclosure include a progressive reduction in the microbial count as the result of the application of a photon MPA enhanced antimicrobial oxidizing agent solution. This is accomplished by utilizing an antimicrobial oxidizing agent solution that has been enhanced with photons and phonons to increase its effectiveness. According to various embodiments, the wavelength of the photons is from 0.001 nm to 845 nm. In various embodiments, the wavelength of the photons and or phonons is 0.01 nm to about 400 nm, about 300 nm to about 845 nm, or any combination of wavelengths thereof.

According to various embodiments of the disclosure, the wavelengths that dissociate trioxygen maybe excluded from the photons before transmission to the target where the desired interaction is to take place with the oxidizing agent. In various embodiments, one or more of trioxygen, oxygen, and hydrogen are generated when the oxidizing agent is exposed to the photons and or phonons and creates a self-sustaining circuit of reactions that generates electronically modified oxygen derivatives as long as conditions allow. Various embodiments utilize hydrogen peroxide as an oxidizing agent in liquid form and ambient air as a gas. In various embodiments, the described reactions take place with reactants in different states of matter.

In an example embodiment of a system for progressive reduction of the microbial count in ambient air, a room with 1,000,000 colony forming units (CFUs) is equipped with a system for performing the methods as disclosed herein. A small micron photon/phonon enhanced antimicrobial dry fog of an enhanced oxidizing agent is continuously administered into the ambient air through an existing HVAC system at a concentration of less than 1 part per million. This low concentration causes a reduction in the microbial CFUs as the small micron dry fog slowly settles through the ambient air killing CFUs at a rate of about 20%. After 20 minutes, the continuously administered small micron photon/phonon MPA enhanced antimicrobial oxidizing agent fog reduces the 1,000,000 CFUs by 20% to 800,000 CFUs. As the progressive regression continues, the CFU count drops and after 1 hour of continuous treatment the CFU count is at 512,000. With continued progressive regression, there are 262,144 CFUs in the ambient air after 2 hours and 134,217 CFUs after 3 hours. The ambient air continues to get cleaner and cleaner and after 5 hours the progressive regression of the microbial count with an embodiment of this system of small micron photon and or phonon enhanced antimicrobial oxidizing agent dry fog with a photon/phonon MPA enhanced oxidizing agent has reduced the CFU count to 35,184 CFUs. By continuing this reaction out for 8 hours, the CFU count is reduced to 4772 CFUs. That's a 99.5% reduction in the microbial count in the ambient air over an 8 hour period utilizing a progressive regression of microbes achievable with embodiments of the methods described in the present disclosure. In contrast, independent research lab testing shows little or no microbial reduction with 1 part per million of standard hydrogen peroxide with a 5 minute contact time. The same lab study shows over a 5 log reduction in microbial counts with the photon/phonon enhanced oxidizing agent (hydrogen peroxide) solution described in embodiments of the present disclosure.

Embodiments of the present disclosure have numerous applications across many industries, from energy storage and production, medical, food, environmental, and others. Embodiments of the method of combining photocatalytic, photochemicallytic (photochemical and photocatalytic), and dissociation reactions with photon MPA emission enhanced oxidizing agents open a new frontier. Conventional photocatalysis decomposes oxidizing agents by disproportionation and by promoting oxidizing agent reduction instead of hydrogen liberation. Embodiments of the present disclosure report successful examples of oxidizing agent and water dissociation, wherein trioxygen associates with the reactants and suppresses the reactant reduction, thus promoting hydrogen liberation. Various embodiments of an organic photocatalytic system provide a basis of photocatalytic and photochemical and photocatalytic oxidizing agent and water dissociation.

An oxidizing agent is a chemical species that undergoes a chemical reaction in which it gains one or more electrons. Also, an oxidizing agent can be regarded as a chemical species that transfers electronegative atoms, usually oxygen, to a substrate.

As used herein, an oxidizing agent can be called an oxygenation reagent or oxygen-atom transfer (OAT) agent. Oxidation reactions may involve oxygen atom transfer reactions and hydrogen atom abstraction which is a reaction where removal of an atom or group from a molecule by a radical occurs. The radiation commonly used in antimicrobial bleaching and other chemical processes is known as UV-C. Ultra-Violet (UV) light is invisible to the human eye and is divided into UV-A, UV-B, and UV-C. UV-C is found within 100-280 nm range. The germicidal action of UV-C is maximized at approximately 265 nm with reductions on either side. UV-C sources typically have their main emission at 254 nm. As a result, germicidal lamps can be effective in breaking down the DNA of microorganisms so that they cannot replicate and cause disease. UV radiation also can be used to eliminate trioxygen which is a Reactive Oxygen Species (ROS). Trioxygen can also be used as a catalyst to convert $H_2O$ to products that exhibit health benefits, antimicrobial properties, bleaching properties, etching properties, and other products that have wide commercial uses. This use of generated Trioxygen in this disclosure is the reason that wavelengths that dissociate trioxygen may be excluded from the wavelengths of the applied photon emissions.

As used herein, photocatalysis is the acceleration of a photoreaction in the presence of a catalyst. Photocatalysts are materials that change the rate of a chemical reaction on exposure to photons of certain wavelengths. In catalyzed photolysis, photons are absorbed by a substrate. Photocatalytic activity (PCA) depends on the ability of the catalyst to create electron-hole pairs, which utilize electronically modified oxygen derivatives, which are then able to undergo secondary reactions. Typically, two types of photocatalysis reactions are recognized, homogeneous photocatalysis and heterogeneous photocatalysis. As used herein, when both the photocatalyst and the reactant are in the same phase, i.e., gas, solid, or liquid, such photocatalytic reactions are termed as homogeneous photocatalysis. As used herein, when both the photocatalyst and reactant are in different phases, such photocatalytic reactions are classified as heterogeneous photocatalysis. When a photocatalyst is exposed to photon of the desired wavelength (and sufficient energy), the energy of photons and or phonons is absorbed by an electron ($e^-$) of valence band and it is excited to conduction band. In this process, a hole ($h^+$) is created in valence band. This process leads to formation of the photoexcitation state, and a $e^-$ and $h^+$ pair is generated. When hydrogen peroxide is involved in PCA a hydroxyl radical is generated in both types of reactions. The difference in the two types of photocatalytic reactions are the forms and placements of the reactants and the photocatalysts.

An example of the described reaction used as a bleaching method can be illustrated with the preparation of wood pulp as used in paper manufacturing. One of the largest volume uses of hydrogen peroxide worldwide is in the paper industry. Hydrogen peroxide is used to increase the brightness of deinked pulp. The bleaching methods are similar for mechanical pulp in which the goal is to make the fibers brighter. By using various embodiments of the reaction described herein and enhancing the hydrogen peroxide with photons and or phonon with a wavelength of 0.001 nm to 845 nm, a synergistic reaction takes place generating ROS and EMODs and produces photo-oxidation products, photocatalytic products, and/or photochemical products by photon absorption by the oxidizing agent and target, wherein the produced photo oxidation products, photocatalytic products, and/or photochemical products cause a greater bleaching result when the same concentration of oxidizing agent is used, or allow for the same bleaching effect with a lower concentration of oxidizing agent. According to various embodiments, the self-sustaining circuit of reactions where the wavelengths that dissociate trioxygen are excluded from the photon emission permits a reaction that has not been described or utilized with a bleaching reaction previously.

Hydrogen peroxide is also used widely in the petroleum and petrochemical industries. An example is in the production of plastics. Propylene oxide (PO), an important bulk chemical intermediate, is used for the manufacturing of polyurethanes (polyether polyols), polyesters (propylene glycol) and solvents (propylene glycol ethers). Hydrogen peroxide dissociates generating hydroxyl radicals that react with propylene to form PO. According to various embodiment, the methods described in the present disclosure generate more hydroxyl radicals by exposing hydrogen peroxide to photon emissions of 0.001 nm-845 nm with the wavelengths that dissociate trioxygen excluded. This "enhanced" hydrogen peroxide is more reactive in generating PO then un-enhanced (standard) hydrogen peroxide. The self-sustaining circuit of reactions where the wavelengths that dissociate trioxygen are excluded from the photon emission permits an enhanced reaction that has not been described or utilized with common reactions currently utilized in industries like the petroleum/petrochemical industries.

Hydrogen peroxide ($H_2O_2$) is commonly used in the dairy industry as an antimicrobial preservative. By enhancing its effectiveness with various embodiments of the methods described in the present disclosure, hydrogen peroxide exposed to photon emissions of 0.001 nm-845 nm with the wavelengths that dissociate trioxygen excluded generates more hydroxyl radicals and other EMODs that exert a greater preservative and antimicrobial effect than un-enhanced $H_2O_2$.

Oxidizing agents are also used in the production of electronics such as microprocessors. By enhancing its effectiveness with various embodiments of the methods described in the present disclosure, hydrogen peroxide and other oxidizing agents exposed to photon emissions of 0.001 nm-845 nm with the wavelengths that dissociate trioxygen excluded generates more hydroxyl radicals and other EMODs. This allows for a lower concentration of $H_2O_2$ to provide the required quantity of ROS needed to etch circuit boards and other uses common in the electronics industry.

The list of industries that utilize oxidizing agents and the ROS/EMODs that they provide is extensive. The applications and embodiments described herein are meant to provide examples but are not meant to limit the scope of the disclosure. In addition, a partial list of oxidizing agents includes oxygen ($O_2$), trioxygen ($O_3$), hydrogen (H), hydrogen peroxide ($H_2O_2$), inorganic peroxides, Fenton's reagent, fluorine ($F_2$), chlorine ($Cl_2$), halogens, nitric acid ($HNO_3$), nitrate compounds, sulfuric acid ($H_2SO_4$), peroxydisulfuric acid ($H_2S2O_8$), peroxymonosulfuric acid ($H_2SO_5$), sulfur compounds, hypochlorite, chlorite, chlorate, perchlorate, halogen compounds, chromic acid, dichromic acid, chromium trioxide, pyridinium chlorochromate (PCC), chromate, dichromate compounds, hexavalent chromium compounds, potassium permanganate ($KMnO_4$), sodium perborate, permanganate compounds, nitrous oxide ($N_2O$), nitrogen dioxide/dinitrogen tetroxide ($NO_2/N_2O_4$), urea, potassium nitrate ($KNO_3$), sodium bismuthate ($NaBiO_3$), ceric ammonium nitrate, ceric sulfate, cerium (IV) compounds, peracetic acid, and lead dioxide ($PbO_2$). This list is meant to serve as an example but is not inclusive of all oxidizing agents.

To monitor the synergistic reaction described in the present disclosure, various embodiments include at least one or more sensors or other devices to indicate, detect, or inform of one or more of the following properties of the target or storage or environment: pH, temperature, salinity, density, trioxygen concentration, oxygen concentration, hydrogen concentration, oxidizing agent concentration, flow rate, microbial content, presence or absence of bacterial species, presence or absence of corrosive metabolites or otherwise corrosive substance, identification of a gas, presence or absence of an aqueous environment, presence or absence of high, low, or otherwise concentration of bacterial or non-bacterial, biomass or non-biomass, microbial content, or location of biofilms may be used. This list is not all inclusive but is meant to provide examples of sensors and other devices that may be used singularly or in multiples. According to various embodiments, these sensors may be used to help regulate the reactions described herein.

Temperature affects reaction rate as some of the reactions described herein are exothermic. A high pH favors hydroxyl radical formation at the expense of trioxygen formation. A low pH favors trioxygen formation over hydroxyl radical production. According to various embodiments, flow rate is used to influence the effects of the reaction by altering the amount of time substances are exposed to the photon and or phonons. Also, in various embodiments, flow rate is used to modulate exposure to variables such as temperature, flow rate, microbes, humidity, and other conditions. This list is not inclusive but is meant as an example of effects of variables.

In some embodiments, variables such as photon and or phonon emissions are used to affect the generation of ROS. These emissions can be less than 1 second in duration if the intensity of the emissions is high or the time of the applied emissions can be perpetual if the dose or intensity of the emissions is low. In some embodiments, the temperature of the reaction not only affects the reaction rate but is also used to modulate enzymes present in the reactants. An example of this is the enzyme catalase. Catalase can hinder or stop reactions utilizing oxidizing agents by inactivating hydroxyl radicals. Catalase is inactivated by temperatures above certain limits. By using a sensor to measure temperature and by varying the temperature of the oxidizing agent and or the reactants enzymes such as catalase can have their effects modulated.

According to various embodiments, the photon/phonon generating apparatus used in the methods described herein is located in or adjacent to the oxidizing agent to be enhanced. In some instances, the photon/phonon generating apparatus is located further from the oxidizing agent and methods of transmission of the photons and or phonons are utilized. These methods of transmission include fiber optics and other conductive media.

With an increase in temperature (more phonons), there is an increase in the number of collisions between reactants. Increasing the concentration of a reactant increases the frequency of collisions between reactants and will, therefore, increase the reaction rate. An increase in temperature corresponds to an increase in the average kinetic energy of the particles in a reacting mixture—the particles move faster, colliding more frequently and with greater energy. Increasing concentration tends to also increase the reaction rate. A decrease in temperature may have the opposite effect when compared to an increase in temperature.

The rate, or speed, at which a reaction occurs depends on the frequency of successful collisions. A successful collision occurs when two reactants collide with enough energy and with the right orientation. That means if there is an increase in the number of collisions, an increase in the number of particles that have enough energy to react, and/or an increase in the number of particles with the correct orientation, the rate of reaction will increase.

The rate of reaction is related to three factors: collision frequency, collision energy, and geometric orientation. The collision frequency is dependent, among other factors, on the temperature of the reaction. When the temperature is increased, the average velocity of the particles is increased. The average kinetic energy of these particles is also increased. The result is that the particles will collide more frequently, because the particles move around faster and will encounter more reactant particles. However, this is only a minor part of the reason why the rate is increased. Just because the particles are colliding more frequently does not mean that the reaction will occur.

Another effect of increasing the temperature is that more of the particles that collide will have the amount of energy needed to have an effective collision. In other words, more particles will have the necessary activation energy. For example, at room temperature, the hydrogen and oxygen in the atmosphere do not have sufficient energy to attain the activation energy needed to produce water:

Average room temperature+$O_2(g)$+$H_2(g)$→No reaction

At any one moment in the atmosphere, there are many collisions occurring between these two reactants. But what we find is that water is not formed from the oxygen and hydrogen molecules colliding in the atmosphere, because the activation energy barrier is just too high, and all the collisions are resulting in rebound. When we increase the temperature of the reactants or give them energy in some other way, the molecules have the necessary activation energy and are able to react to produce water:

$$\text{Sufficient energy} + O_2(g) + H_2(g) \rightarrow H_2O(l)$$

In various embodiments, the rate of a reaction, by design, is slowed down. In some embodiments, lowering the temperature is used to decrease the number of collisions that would occur and lowering the temperature would also reduce the kinetic energy available for activation energy. If the particles have insufficient activation energy, the collisions will result in rebound rather than reaction. Using this idea, when the rate of a reaction needs to be lower, keeping the particles from having sufficient activation energy will keep the reaction at a lower rate.

In various embodiments, the humidity where the reactions described herein takes place affects the evaporation rate of the droplet if the desired location of the reaction is in the air. This variable, humidity, can change the rate of evaporation if the humidity is high and cause a decrease in the evaporation rate or cause an increase in the evaporation rate if the humidity is low in the area where the reactions described herein is to take place.

In various embodiments, where the reactions described herein take place in a liquid or gaseous environment, the opacity of the liquid or gas affects the reaction rate. In some embodiments, the more opaque a liquid or gas is, a higher dose of photons and or phonons is required to achieve the desired reaction rate due to the opacity of the medium and its ability to affect the transmission of the photon/phonon emissions. Likewise, in some embodiments, the viscosity of the medium where the described reaction takes place influences the reaction rate. In some embodiments, a higher viscosity medium retards the reaction rate due to the loss of photon/phonon energy as the photons and or phonons move through the medium. In other embodiments, a lower viscosity medium causes the photons and or phonons to lose less energy as they move through the medium.

In some embodiments, the reactions described herein have an increased reaction rate with the addition of a catalyst. For example, iron oxides catalyze the conversion of hydrogen peroxide into oxidants capable of transforming recalcitrant contaminants. This is an example of an additive effect of a catalyst.

In some embodiments, it is desirable to slow down or halt the described reaction. For example, peroxidases or peroxide reductases are a group of enzymes which play a role in various chemical processes. They are named after the fact that they commonly break up peroxides.

Flocculants, also known as clarifying agents, are used to remove suspended solids from liquids by inducing flocculation. The solids begin to aggregate forming flakes, which either precipitate to the bottom or float to the surface of the liquid, and then they can be removed or collected. According to various embodiments, flocculants are added to the reactions described herein before during or after the photon/phonon enhanced oxidizing agent is applied to the target where the described reaction is to take place. In some embodiments, flocculants are added before the reaction to remove substances that are not desired to undergo the described reaction. In other embodiments, the flocculant is added during the reaction or after the reaction depending on the desired outcome and use of the precipitated substance.

FIG. 1 is an exemplary diagram showing that a reaction can occur from a reactant molecule via an intermediate such as hydroperoxyl to form a trioxygen molecule. FIG. 1 also displays an exemplary diagram showing a "stored" oxidizing effect that can be tapped to provide reactive oxygen species as needed. The "stored" oxidizing effect feeds the self-sustained circuit of reactions so that hydrogen and its ions, oxygen and its ions, trioxygen, hydroperoxyls, hydrons, reactive oxygen species and other products are generated until one of the reactants is depleted. During its decay back to the ground state, the trioxygen molecule created in the described reaction emits energy by breaking bonds in the reactants. This released energy from the endogenous x-ray photons released provides photons and/or phonons to help power the continuing self-sustaining circuit of reactions.

Radiation of 0.01 nm through 845 nm emitted on water and hydrogen peroxide creates the reaction illustrated in FIG. 1. Once the reaction is initiated, the reaction proceeds with or without further radiation exposure due to endogenous x-ray photons produced. The products such as trioxygen, hydrogen, oxygen and other generated electronically modified oxygen derivatives continue to "power" the reaction. An example of these products contributing to the continued reaction can be found in the decay of trioxygen. As it decays and interacts with reactants, photons and phonons are produced releasing energy to the reaction.

FIG. 2 illustrates the enhanced effectiveness produced by an embodiment of the reactions illustrated in FIG. 1. The control substance (3% hydrogen peroxide without photon exposure) exhibited a 0.0% microbial (*E. coli*) reduction while the samples of the photon enhanced solution displayed a heightened effectiveness of microbial reduction within minutes after receiving a 2 minute exposure of photons from the wavelengths from 0.001 nm-845 nm. This increased effectiveness was still evident at 4 weeks post exposure to photons of 0.01 nm through 845 nm. This heightened residual effect supports the claim of continuing self-sustaining circuit of reactions.

Various embodiments of the present disclosure relate to producing one or more of trioxygen, hydrogen and/or its isotopes, oxygen and/or its isotopes, hydrons, hydroperoxyls and/or electronically modified oxygen derivatives, reactive oxygen species, free radicals, oxidizing molecules, oxygen-atom transfer (OAT) agents, oxidizing agents and/or various related species from oxidizing agents that are exposed to certain wavelengths of photon/phonon emission, exposed for certain amounts of time and exposed to certain intensities of photon/phonon emission. In various embodiments, the oxidizing agents are exposed to multiple frequencies of photon/phonon emission and multiple exposures of photon/phonon emission. In embodiments, the photons and or phonons are supplied to the oxidizing agents continuously or in bursts or pulses. A continuous photon/phonon emission could be, for example, from a light emitting diode suspended in a container of an oxidizing agent emitting a constant dose of photons and or phonons. Bursts or pulses of photon/phonon emission could be utilized to rapidly enhance an oxidizing agent with 0.01 nm-845 nm photon/phonon emissions. For example, from a high intensity laser where the high intensity bursts or pulses may be only seconds in duration, but these bursts or pulses could provide the same dose of photon/phonon emissions as a long duration continuous photon/phonon emission that was at a low dose, where dose is defined as intensity of the photon/phonon emission times the time of application.

The present disclosure describes research into the effects of photons and phonons on oxidizing agents, and a discovery that offers a revolutionary and multi-disciplinary advancement to science. The disclosed methods provide a new paradigm to perform photocatalytic oxidation of substrates using photon/phonon emission as energy input, generating endogenous photons and or phonons and producing trioxygen, hydrons, hydroperoxyls, oxygen and its ions, and/or hydrogen and its ions as the catalysts, oxidizing agents as the oxygen source, and dissociation reactions to minimize hindrances to the reactions.

Photocatalytic activity (PCA) is commonly applied to a target where the desired reaction is to take place in two distinct ways. Various embodiments of the present disclosure utilize both methods of applying photocatalytic activity to generate unique reactions that continue even after the photon/phonon emissions that initiates the PCA is discontinued. As detailed in the present disclosure, it has been found that the destruction of trioxygen ($O_3$) by certain wavelengths of photon emission prevents or retards reactions involved in the photocatalytic effects. The catalyst, trioxygen, was being eliminated by certain wavelengths of photon that encourage dissociation reactions. By altering the production or availability of trioxygen, according to embodiments of this disclosure, the reaction includes steps that allow and encourage, or alternatively prevent or retard the generation of products such as oxygen, hydrogen, electronically modified oxygen derivatives (EMODS), and others. Some examples of EMODs are superoxide, hydrogen peroxide, hydroxyl radical, hydroxyl ion, and nitric oxide.

These EMODs are generated by exposing oxidizing agents to radiation of a certain wavelength, for example residual effect which, shown in Table 2, has shown as an increased effect that lasts for days, thereby providing a Photon Augmented Oxidizing Agent (PAOA). The expected life span of EMODs when they are found naturally in nature is measured in nanoseconds. Exposing oxidizing agents to photons from 0.01 nm-845 nm produces a PAOA having a unique EMOD composition that exhibits a residual effect demonstrated by its existence for hours, days, weeks, and greater extended periods of time. In various embodiments, the radiation wavelength in a range of 0.01 nm to 845 nm is produced from a variety of sources such as LEDs, lasers, natural light, electromagnetic radiation, arc lamps and other suitable sources. The list of radiation producing sources is not meant to limit sources to those listed but to serve as an example.

Table 2 shows actual testing results that illustrate the residual effect of PAOAs containing EMODs created by embodiments of the present disclosure. The test substance was a solution of 3% hydrogen peroxide, which was exposed to photons with wavelengths from 0.01 nm-845 nm for 2 minutes to form the PAOA containing EMODs. The test substance or PAOA was applied to target, which included a carrier with a viable bacteria concentration of anaerobic bacteria *Staphylococcus epidermidis* ATCC 12228, where, based on Table 1, the control is the same microbe. The PAOA was applied 1 minute, 5 minutes, 10 minutes, 30 minutes, 1 hour, 12 hours, 24 hours, 2, days, 5 days, and 7 days after photon exposure. In one test, after 7 days, the PAOA was again subjected to photon exposure of from 0.01 nm-845 nm for 2 minutes for reactivation. This demonstrated an increased effectiveness over the PAOA that had been exposed to photon emissions 7 days previously. This is another example of the effectiveness of the photons ability to increase the effectiveness of the oxidizing agent.

TABLE 2

| Microorganism | Test Substance Concentration | Time After Radiation Exposure Substance Applied to Carrier | CFU/carrier | Percent Reduction vs. Parallel Control | Log10 Reduction vs. Parallel Control |
|---|---|---|---|---|---|
| *S. epidermidis* ATCC 12228 | Control | N/A | 6.04E+05 | N/A | N/A |
| | 3% $H_2O_2$ | 1 Minute | 7.00E+04 | 88.42% | 0.94 |
| | | 5 Minute | 7.00E+04 | 88.42% | 0.94 |
| | | 10 Minute | 3.10E+04 | 94.87% | 1.29 |
| | | 30 Minute | 2.80E+04 | 95.37% | 1.33 |
| | | 1 Hour | 7.10E+04 | 88.25% | 0.93 |
| | Control | | 9.20E+04 | N/A | N/A |
| | 3% $H_2O_2$ | 12 Hours | 1.80E+04 | 80.43% | 0.71 |
| | Control | | 1.33E+05 | N/A | N/A |
| | 3% $H_2O_2$ | 24 Hours | 2.10E+04 | 84.21% | 0.80 |
| | Control | | 3.00E+05 | N/A | N/A |
| | 3% $H_2O_2$ | 2 Days | 9.00E+04 | 70.00% | 0.52 |
| | Control | | 4.50E+04 | N/A | N/A |
| | 3% $H_2O_2$ | 5 Days | 3.29E+03 | 92.69% | 1.14 |
| | Control | | 9.80E+04 | N/A | N/A |
| | 3% $H_2O_2$ | 7 Days | 1.50E+04 | 84.69% | 0.82 |
| | 7 Days w/Reactivation | | 1.00E+04 | 89.80% | 0.99 | between 0.001 nm and 845 nm, where the interaction of these agents, oxidizing agents and photons, when combined produce a total effect that is greater than the sum of the effects of the individual agents. The wavelength range utilized in this disclosure was selected based on testing that showed x-ray photons of 0.01 nm produced the effects of this disclosure as well as photons with wavelengths through 845 nm. This photon exposure generates EMODs that last longer than typically found in nature by evidence of a There are statistical variations but when comparing the increased activation of the PAOAs at 1 minute post augmentation with PAOA that was augmented 7 days previously, the results are very similar. The PAOA exhibits a pronounced residual effect. This residual effect is evidenced by the increased antimicrobial effect of the PAOAs. The un-augmented oxidizing agents have been shown to exhibit an antimicrobial effect of approximately 30% at a dwell time of 5 minutes. The application of photon emissions only (no oxidizing agent) of between 0.01 nm and 845 nm has been shown to kill approximately 1% of the microbes that are exposed to it for 5 minutes. The PAOAs demonstrate an antimicrobial effect greater than un-augmented (control) oxidizing agents which showed no microbial reduction. This effect provides a concentration of an oxidizing agent with a vastly greater antimicrobial effect or a concentration of PAOA can be utilized that is a much lower concentration than the un-augmented oxidizing agent and exhibit the same antimicrobial activity.

Table 3 shows additional testing results that illustrate the residual effect of PAOAs containing EMODs created by embodiments of the present disclosure. The test substance was hydrogen peroxide at 1 ppm and at 0.3%, which was exposed or not exposed to photons with a wavelength from 0.001 nm-845 nm and applied to target, which included a biological medium inoculated with a viable bacteria concentration of *Staphylococcus aureus* ATCC 6538. Further, it may be appreciated that the control is the same microorganism.

in which trioxygen decreases by first order kinetics. In various embodiments, dependent on the pH, viscosity, opaqueness and other qualities previously explained relating to the composition of the liquids, the half-life of trioxygen is in the range of seconds to hours. In various embodiments, factors influencing the decomposition of trioxygen in liquids are temperature, pH, ions, cations, environment, concentrations of dissolved matter, and photon/phonon emissions. As disclosed above, trioxygen decomposes partly in the presence of hydroxyl radicals. In various embodiments, when the pH value increases, the formation of hydroxyl radicals increases in a substance. In a solution with a high pH value, there are more hydroxide ions present, see Reaction 1 and Reaction 2. These hydroxide ions act as an initiator for the decay of trioxygen:

$$O_3 + OH^- \rightarrow HO_2^- + O_2 \quad \text{Reaction 1}$$

$$O_3 + HO_2^- \rightarrow \cdot OH + O_2^{\cdot -} + O_2 \quad \text{Reaction 2}$$

TABLE 3

| Test Microorganism | Contact time | Test Substance | Replicate | CFU/ML | Average CFU/ML | Average percent reduction compared to controls | Average og₁₀ reduction compared to controls |
|---|---|---|---|---|---|---|---|
| S. aureus ATCC 6538 | Pre-Treatment | Numbers Control | 1 | 3.32E+06 | 3.43E+06 | N/A | N/A |
| | | | 2 | 2.90E+06 | 3.43E+06 | N/A | N/A |
| | Pre Treatment | Numbers Control | 1 | 3.90E_06 | 3.43E+06 | N/A | N/A |
| | | | 2 | 3.60E+06 | 3.43E+06 | N/A | N/A |
| | 5 minutes | 1 ppm H2O2 no photon activation | 1 | 4.10E+06 | 4.05E+06 | No reduction | No reduction |
| | 5 minutes | 1 ppm H2O2 no photon activation | 2 | 4.10E+06 | 4.05E+06 | No reduction | No reduction |
| | 5 minutes | .3% H2O2 no photon activation | 1 | 4.10E+06 | 4.05E+06 | No reduction | No reduction |
| | 5 minutes | .3% H2O2 no photon activation | 2 | 4.00E+06 | 4.05E+06 | No reduction | No reduction |
| | 5 minutes | 1 ppm with photon activation | 1 | Less than 1.00E+01 | Less than 1.00E+01 | Greater than 99.997% | Greater than 5.54 |
| | 5 minutes | 1 ppm with photon activation | 2 | Less than 1.00E+01 | Less than 1.00E+01 | Greater than 99.997% | Greater than 5.54 |
| | 5 minutes | .3% with photon activation | 1 | Less than 1.00E+01 | Less than 1.00E+01 | Greater than 99.997% | Greater than 5.54 |
| | 5 minutes | .3% with photon activation | 2 | Less than 1.00E+01 | Less than 1.00E+01 | Greater than 99.997% | Greater than 5.54 |

In an exemplary embodiment, it is understood that after trioxygen is produced it will decay rapidly, because trioxygen is an unstable compound with a relatively short half-life. The half-life of trioxygen in liquid is shorter than in air. Trioxygen decays in liquids partly in reactions with hydroxyl radicals. The assessment of a trioxygen decay process involves the reactions of two species: trioxygen and hydroxyl radicals. As used herein, when these hydroxyl radicals are the dominant particles in the solution, it is called herein an advanced oxidation process (AOP).

According to various embodiments, the decay of trioxygen in contact with hydroxyl radicals is characterized by a fast initial decrease of trioxygen, followed by a second phase According to various embodiments, the radicals that are produced during Reaction 2 introduce other reactions with trioxygen, causing more hydroxyl radicals to be formed. In various embodiments, dependent on the nature of dissolved matter in a liquid, these can accelerate or slow down the decay of trioxygen. Trioxygen reacts with organic matter. This reaction with organic matter depletes the concentration of trioxygen. The presence of organic matter accelerates the decay of trioxygen by its consumption in reactions with organic matter. Inversely, in solutions with little or no organic matter, trioxygen remains available for reactions displayed in this disclosure. Substances that accelerate this reaction are called promoters and substances that slow down the reaction are called inhibitors. When a liquid is infused with trioxygen, the term "scavenging capacity" is used herein in reference to the decay rate of the trioxygen. Scavengers and inhibitors are entities that react with hydroxyl radicals and slow down the reaction between trioxygen and hydroxyl radicals. In various embodiments, methods of inhibiting the decay of trioxygen involve altering the pH of the target liquid and using deionized solutions as dilutants when possible.

In further exemplary embodiments, oxidative reactions due to photocatalytic, homogenous effects are described and utilized as follows:

The mechanism of hydroxyl radical production follow paths such as:

$$O_3 + h\nu \rightarrow O_2 + O \quad \text{Equation 1}$$

$$O + H_2O \rightarrow .OH + .OH \quad \text{Equation 2}$$

$$O + H_2O \rightarrow H_2O_2 \quad \text{Equation 3}$$

$$H_2O_2 + h\nu \rightarrow .OH + .OH \quad \text{Equation 4}$$

Similarly, the Fenton system produces hydroxyl radicals by the following mechanism:

$$Fe^{2+} + H_2O_2 \rightarrow HO. + Fe^{3+} + OH— \quad \text{Equation 5}$$

$$Fe^{3+} + H_2O_2 \rightarrow Fe^{2+} + HO.2 + H+ \quad \text{Equation 6}$$

$$Fe^{2+} + HO \rightarrow Fe^{3+} + OH— \quad \text{Equation 7}$$

In photo-Fenton type processes, additional sources of OH radicals are considered: through photolysis of $H_2O_2$, and through reduction of $Fe^{3+}$ ions under photon/phonon excitation:

$$H_2O_2 + photons \rightarrow HO. + HO. \quad \text{Equation 8}$$

$$Fe^{3+} + H_2O + photons \rightarrow Fe^{2+} + HO. + H+ \quad \text{Equation 9}$$

Oxidative reactions due to photocatalytic heterogenous effect:

$$h^+ + H_2O \rightarrow H^+ + .OH \quad \text{Equation 10}$$

$$2h^+ + 2H_2O \rightarrow 2H^+ + H_2O_2 \quad \text{Equation 11}$$

$$H_2O_2 \rightarrow 2.OH \quad \text{Equation 12}$$

The reaction of $H_2O_2 = H_2O + O$ is typically referenced in literature as the predominant disassociation reaction associated with hydrogen peroxide and results in the production of oxygen and water. There are several reaction pathways such as dissociation to hydronium ion and hydroperoxide, and disproportionation to dioxygen and water. Note that trioxygen is not produced in the above reactions.

According to various embodiments, trioxygen is photo-dissociated by certain wavelengths of photon emissions. In various embodiments, while trioxygen is created, it is also dissociated depending on the desired outcome of the reaction. Table 4 is a partial list of the products of trioxygen dissociation, and a partial list of the wavelengths associated with those products.

TABLE 4

| | |
|---|---|
| $O(^3P) + O_2(^3\Sigma)$ | 1118 nm-1119 nm |
| $O(^3P) + O_2(^1\Delta)$ | 599 nm-600 nm |
| $O(^3P) + O_2(^1\Sigma)$ | 452 nm-453 nm |
| $O(^1D) + O_2(^3\Sigma)$ | 402 nm-403 nm |
| $O(^1D) + O_2(^1\Delta)$ | 307 nm-308 nm |
| $O(^1D) + O_2(^1\Sigma)$ | 263 nm-264 nm |
| $O(^3P) + O(^3P) + O(^3P)$ | 197 nm-198 nm |

According to various embodiments, in one path, the embodiments describe one or more reactions whereby the trioxygen is not totally or is partially photo-dissociated by photon emissions. Trioxygen then becomes a photocatalyst for new reactions. In various embodiments, trioxygen is produced and retained when the wavelengths of photodissociation (e.g., Table 4) are excluded. This exclusion coupled with photocatalytic reactions generating one or more of trioxygen, hydrogen and/or its isotopes, oxygen and/or its isotopes, electronically modified oxygen derivatives, reactive oxygen species, free radicals, oxidizing molecules, oxidizing agents, and/or various related species from oxidizing agents that are exposed to certain frequencies of photon emissions. In various embodiments, the reaction with OH— is the initial decomposition step of trioxygen decay, the stability of a trioxygen solution is thus dependent on pH and varies with variations in pH. In various embodiments, at pH above 8 the initiation rate, in the presence of radical scavengers, is generally proportional to the concentrations of trioxygen and OH—. In other embodiments, in acidic solutions the reaction with OH— is not the initiation step. Predicted reaction rates below pH 4 including a mechanism based only on reaction with OH— are much lower than those determined experimentally. The trioxygen equilibrium reaction below becomes significant and the initiation reaction is catalyzed.

$$O_3 \underset{k_{-17}}{\overset{k_{17}}{\rightleftharpoons}} O + O_2$$

$$k_{17} = 10^{-7} s^{-1}$$

$$k_{-17} = 4 \cdot 10^9 M^{-1} s^{-1}$$

The atomic O continues to react with $H_2O$, or forms an excited trioxygen radical, from recombination, that subsequently reacts with $H_2O$, as shown in the two equations below, respectively.

$$O + H_2O \rightleftharpoons 2 HO^\bullet$$

$$O_3^\bullet + H_2O \rightleftharpoons H_2O_2 + O_2$$

In various embodiments, the species formed then react further, forming other radicals such as $O_2—/HO_2$. The propagating products, HO. and $HO_2$, diffuse and react with trioxygen in the continuing self-sustaining circuit of reactions. Only low concentrations of the terminating species are present in the solution which is why the significant part of the termination reactions below also takes place.

$$HO^\bullet + HO^\bullet \overset{k_{20}}{\rightleftharpoons} H_2O_2$$

$$k_{20} = 6 \cdot 10^9 M^{-1} s^{-1}$$

$$HO^\bullet + HO_2 \overset{k_{21}}{\rightleftharpoons} H_2O + O_2$$

$$k_{21} = 7 \cdot 10^9 M^{-1} s^{-1}$$

$$HO_2 + HO_2 \overset{k_{22}}{\rightleftharpoons} H_2O_2 + O_2$$

$$k_{22} = 8 \cdot 10^5 M^{-1} s^{-1}$$

An example of an oxidizing agent involved in this reaction: $H_2O_2$+photon emissions from 0.001 nm to 845 nm, where the wavelengths causing photodissociation of trioxygen have been excluded, when $H_2O_2$ and this selective photon emission are combined, this reaction yields $H_2+2HO_2$ which in turn yields $H_2O$+trioxygen. In various embodiments, this self-sustaining circuit of reactions will continue as long as the correct wavelength of photons are present and $H_2O_2$ (oxidizing agent) is present. Additionally, in some embodiments, it may be appreciated that photons contain heat and can be utilized to vary temperature. In various embodiments, the two paths of this reaction yield various products but particularly $H_2$ and $O_2$ or yield $2HO_2$. In some embodiments, the trioxygen that is created on this path enters and exists in this self-sustaining circuit of reactions with $H_2O$. The self-sustaining circuit of reactions continue to function and is dependent on the supply of trioxygen or hydroperoxyls generated from reactions of trioxygen or hydroxyl radicals or generated from reactions of trioxygen with other reactants. In various embodiments, a self-sustaining circuit of reactions includes numerous reactions and potential reactions that vary depending on variables such as temperature, pH, catalysts, and others. An exemplary reaction is the self-sustaining circuit of reactions where trioxygen reacts with water producing at various stages O2, hydroxyls, H2, HO3, HO4, and hydroperoxyls.

Exposure of oxidizing agents such as hydrogen peroxide with the entire UV spectrum of photon emissions produces hydroxyl radicals but limited or no trioxygen due to the wavelengths that are present that also destroy trioxygen. This dissociation of trioxygen was previously undiscovered or unappreciated and, without this photon exposure consideration, the products of this reaction may not be produced in a self-sustaining circuit of reactions. Furthermore, if this step is performed, but performed in the wrong sequence, the reaction will not have the desired results and the self-sustaining chain of reactions may not occur. Hydroxyl radicals are very reactive free radicals, but they only exist for extremely brief periods of time measured in nanoseconds. This nanosecond long existence leads to a short-term effect whereby the hydroxyl radicals exert an influence that cannot be stored or held in reserve.

According to various embodiments, the production of trioxygen by the photon/phonon emissions and interaction with oxidizing agents with photons of certain wavelengths between 0.01 nm and 845 nm (where 0.01 nm represents the lower range of x-ray photons and 845 nm represents the upper range of photons that dissociate water) but that exclude those wavelengths associated with the dissociation of trioxygen, produces reactants such as hydroperoxyls that react to form trioxygen. With trioxygen in a self-sustaining circuit of reactions, a steady stream of products is created, one being a chain of hydroxyl radicals that can now exert a more long-lasting effect. In various embodiments, this self-sustaining circuit of reactions allows for a "shelf life" where the reaction is maintained and stored for future use even after the photon/phonon exposure to the oxidizing agent has been terminated. In some embodiments, an increased reaction potential that can now be measured in minutes, hours, or days due to the continued effect of the reaction products created.

According to various embodiments, in reference to the disclosed reactions, the embodiments explain new discoveries whereby the photon/phonon emissions directed at the oxidizing agent or oxidizing agents alters the typical reactions. This is accomplished by excluding wavelengths of photon/phonon emissions that inhibit the formation of trioxygen or wavelengths that destroy trioxygen. This creates and allows trioxygen to function as a photocatalyst.

The following embodiment relates to a working model of the equation for the self-sustaining circuit of reactions. In chemical kinetics, an equation dictates that a chemical reaction utilizing oxidizing agents proceeds via a decomposition reaction where an electron induced decomposition by photons and or phonons (excluding wavelengths inhibiting trioxygen formation or destroying trioxygen) of the oxidizing agent proceeds. X defines potential decomposition by-products such as, hydroxyls, hydroperoxyls, hydrons, electronically modified oxygen species, hydrogen, oxygen, and others. In various embodiments, a reaction occurs from a reactant molecule via an intermediate such as hydroperoxyl to form a trioxygen molecule, as shown below.

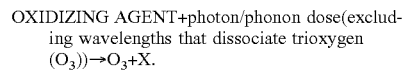

OXIDIZING AGENT+photon/phonon dose(excluding wavelengths that dissociate trioxygen $(O_3)) \rightarrow O_3+X$.

In reference to the above reactions, this embodiment explains discoveries whereby the photon and phonon emissions directed at the oxidizing agent alters the typical reaction. In various embodiments, this is accomplished by excluding wavelengths of photon emissions that inhibit the formation of trioxygen or wavelengths that destroy trioxygen.

Photochemical reactions are a chemical reaction initiated by the absorption of energy in the form of photons and phonons. A consequence of molecules absorbing photons and phonons is the creation of transient excited states whose chemical and physical properties differ greatly from the original molecules. According to various embodiments, photochemical reactions combined with photocatalytic trioxygen generation (PTG) splits water molecules into $H_2$, $O_2$, and $O_3$. PTG can achieve high dissolution in water without other competing gases found in the corona discharge method of trioxygen production, such as nitrogen gases present in ambient air. In various embodiments, this method of generation achieves consistent trioxygen concentration and is independent of air quality because water is used as the source material. Production of trioxygen photochemically was previously not utilized in reactions such as those described in the present disclosure because the required photon wavelength exclusion required to produce trioxygen as compared to producing oxygen as the typical reaction product was not understood or was underappreciated. However, as described herein, in various embodiments it is possible to change the production of oxygen by careful selection of photon wavelengths such that trioxygen is preferentially produced.

Previous research involving UV radiation utilized bulbs (devices emitting electromagnetic energy) produced a bell-shaped curve of radiation that produced wavelengths of dissociation of compounds and wavelengths creating the same compounds. While there may have been a greater influence of either the creation or dissociation wavelength, the resulting reaction was inefficient.

Thus, in various embodiments of the present disclosure, to generate more trioxygen, photochemical reactions combined with PTG, where wavelengths of photons/phonons that dissociate trioxygen are excluded, the dose of photon/phonon emission is increased by increasing the intensity, the time the photon/phonon emission is applied, and other variables, to the dose where some or all variables may be changed to influence the result of the reaction. This demonstrates the nature of the initial complex which decomposes an oxidizing agent upon photon exposure. Further, in various embodiments, multiple reaction sequences are possible. First, comparing the electronic structure of the water and the oxidizing agent molecules, the trioxygen cleaves at least one oxygen-hydrogen bond of the water molecule in a self-sustaining circuit of reactions, which in turn, forms a hydroxyl radical plus atomic hydrogen. In various embodiments, two of the hydroxyl radicals recombine in an exoergic reaction to form an oxidizing agent molecule. The reaction reversibility dictates that upon application of trioxygen to the water molecule, the latter can decompose in one step to form oxygen atoms plus molecular hydrogen. In various embodiments, the oxygen atom in the presence of trioxygen reacts now with a water molecule by an insertion into an oxygen-hydrogen bond to form hydrogen peroxide but with the continued application of trioxygen, the generation of $H_2O_2$ is delayed or excluded. As the reaction is delayed, oxygen and hydrogen are liberated in sufficient quantities to alter the quantity of available components, thus preventing or minimizing the production of $H_2O_2$. Alternatively, in various embodiments, the oxygen atom adds itself to the oxygen atom of the water molecule forming a short-lived intermediate which then rearranges via hydrogen migration to a hydrogen peroxide molecule. The following equations display an electron induced decomposition of two water molecules in proximity $(H_2O(X^1A_1))_2$ to form a hydrogen peroxide molecule while liberating hydrogen and oxygen.

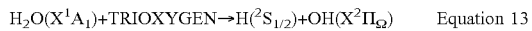  Equation 13

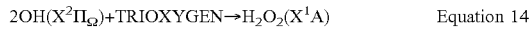  Equation 14

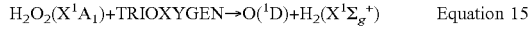  Equation 15

  Equation 16

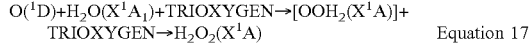  Equation 17

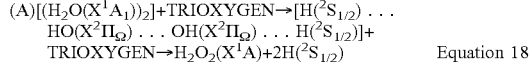  Equation 18

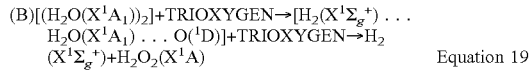  Equation 19

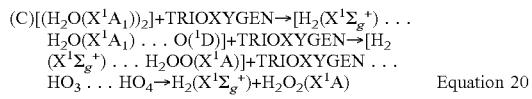  Equation 20

As can be seen above from the equations, the water solution still stores highly reactive radicals such as EMODs, hydroxyl radicals, hydroperoxyls, and the like. In various embodiments, hydroxyl radicals diffuse and once they encounter a second hydroxyl radical, they recombine to form hydrogen peroxide. As described herein, it is understood that upon decomposition of water molecules, oxygen atoms are formed in a first excited state. When the photon/phonon exposure stops and the trioxygen is depleted, the production of excited oxygen atoms ceases too. This reinforces the fact that, without removing the wavelengths that dissociate trioxygen from the photon emissions, this reaction cannot fully proceed as described. The reactivity of ground state atoms with water is different compared to the dynamics of the trioxygen excited counterparts generated during exposure to trioxygen described in the present disclosure via the stated equations.

The data and related discussion on the formation of the hydrogen peroxide molecule also explain the synthesis of atomic and molecular hydrogen during the trioxygen exposure of the oxidizing agent and/or water or solution or combination of solution composition. Here, in various embodiments, the above equations indicate that molecular hydrogen is formed in a one-step mechanism via trioxygen decomposition of the water molecule driven by the trioxygen dose applied to the solution. Alternatively, in various embodiments, the hydrogen atoms formed recombine to form molecular hydrogen. The detection of hydrogen atoms during the trioxygen exposure of the oxidizing agent, water, solution or combination of solution composition phase is a direct proof that the reactions take place. Likewise, the observation of oxygen atoms during the trioxygen exposure suggests that the reactions are also an important pathway of oxygen production. In various embodiments, the matrix reaction solution stores hydrogen as hydronium or other isotopes of hydrogen and as suspended "bubbles" of hydrogen even when the photon/phonon exposure is terminated and trioxygen has ceased to be produced. By placing the reaction solution in a sealed container so that the suspended gases are not allowed to escape, pressure that builds up maintains the reactivity and this potential can be stored for future use.

According to various embodiments, hydroxyl radicals (OH) are formed via a decomposition of a water molecule upon exposure to trioxygen. This trioxygen driven, self-sustaining circuit of reactions generates hydrogen, oxygen, and free radicals, as well as oxidizing molecules including, but not limited to, electronically modified oxygen derivatives, from water or solutions containing oxidizing agents that are exposed to photon emissions which when introduced to an effective amount of a composition containing water and/or an oxidizing agent compound or other compounds or solutions, then exposing the composition to trioxygen, where the composition including the water and/or oxidizing agent compound, solution, or both functions together with trioxygen to lead to a reaction producing hydrogen and/or its isotopes, oxygen and/or its isotopes, electronically modified oxygen derivatives, and/or solutions derived or indirectly derived, resulting from the exposure of the photon emission wavelength(s) in the self-sustaining circuit of reactions. The resultant trioxygen may be used in the self-sustained circuit of reactions. Also, in various embodiments there is a decomposition of the $HO_2$ radical to molecular oxygen plus atomic hydrogen. Finally, to generate the $HO_2$ radical in various embodiments, another reaction is hydrogen atoms reacting with molecular oxygen but with the application of the correct wavelengths of photon and or phonon emissions to the oxidizing agent undergoing this reaction in the self-sustained circuit of reactions, the excited state of produced hydrogen atoms and the produced molecular oxygen and the generation of trioxygen is retarded or stopped by the discontinuance of the photon emissions. In various embodiments, the excited state is preserved by sealing the reactants so that produced gases are maintained, and this allows for the reactive potential to be stored.

The present disclosure describes a significant reaction sequence that has not been previously known, appreciated, or understood. According to various embodiments, by exposing an oxidizing agent to certain doses of photon emissions, hydrogen is liberated from the reaction of the oxidizing agent and photon emissions. In various embodiments, hydroperoxyls are produced and trioxygen is produced when wavelengths of photon emission that dissociate trioxygen are eliminated or reduced in intensity. This reaction generates hydrogen, oxygen, trioxygen, and other free radicals, as well as oxidizing molecules including but not limited to electronically modified oxygen derivatives, from oxidizing agents or solutions containing oxidizing agents that are exposed to certain wavelengths of photon emissions which when introducing an effective amount of a composition contain an oxidizing agent compound or other compounds or solutions, then exposing the composition to photon/phonon emissions of certain wavelengths while excluding the wavelengths from photon emissions that would disallow the formation of trioxygen, wherein the composition containing the oxidizing agent compound, solution or both, functions together with the photon/phonon emissions of certain wavelength or wavelengths to lead to a reaction producing trioxygen, hydrogen and/or its isotopes, oxygen and/or its isotopes, electronically modified oxygen derivatives, and/or solutions derived or indirectly derived resulting from the exposure to photons/phonons of said wavelength(s). The oxidizing potential of trioxygen is slightly less than the oxidizing potential of hydroxyl radicals, but it is greater than the oxidizing potential of hydrogen peroxide. While the commonly accepted lifetime of hydroxyl radicals is a few nanoseconds, trioxygen has been shown to maintain its reactivity for several hours. The ability of trioxygen to linger for an extended period allows for a "stored" oxidizing effect. In various embodiments, the stored oxidizing effect is tapped to provide reactive oxygen species as needed and the stored oxidizing effect feeds the self-sustaining circuit of reactions so that reactive oxygen species are generated until one of the reactants is depleted.

FIG. 2 reflects testing that displays this stored and enhanced oxidizing effect. This is displayed by looking at the 7 day test sample that was treated with PAOA. The continued enhanced antimicrobial effect represents a prolonged antimicrobial effect that has never been demonstrated before with H2O2 that was not exposed to the photons described in this disclosure. When comparing the oxidizing agent control versus the photon/phonon enhanced oxidizing agent solution, there is over a 5-log increase in efficacy with the photon/phonon enhanced oxidizing agent solution as it relates to the antimicrobial effectiveness. By employing the self-sustaining circuit of reactions, embodiments of the disclosure have increased the efficacy and reserved the use of the electronically modified oxygen derivatives that are being continuously generated so that they are available for use over an extended period of time.

The above equations are exemplary and are non-limiting with respect to wavelengths, time of exposure to photon/phonon emissions, intensity of photon/phonon emissions or total dose of photon/phonon emissions. According to various embodiments, by exposing the oxidizing agent or agents to photon emissions from 0.01 nm to 845 nm, where the photon emission of wavelengths that dissociate trioxygen are excluded, a synergistic reaction occurs creating trioxygen and other electronically modified oxygen derivatives and disrupting the typical disassociation reaction of the oxidizing agent or agents. Chemicals such as oxidizing agents exist in a state of flux whereby, they disassociate and reassociate as self-ionization reactions occur.

When alterations of the disassociation reactions occur, new compounds or variations in compound concentrations occur. In various embodiments, these new compounds or variations in compound concentrations created in the photon emission generated synergistic reaction enable a known oxidizing agent to create reactions that have not been observed or reported previously. In various embodiments, by restricting the photon emissions applied to the oxidizing agent so that dissociation of trioxygen is reduced or eliminated, a reaction is produced that has previously not been appreciated or reported. Restricting the dissociation of trioxygen has produced reaction products that have not been described for this reaction previously or that have not been produced in quantities that are shown in the present disclosure.

According to various embodiments of the methods, the reactants may contain enzymes, stabilizers, or other substances that affect the overall reaction rate. Enzymes, stabilizers, and/or other substances can be destroyed or inactivated by temperature variations, pH shifts, and other means. Various embodiments of these techniques are employed to arrive at favorable reaction outcomes. It is understood that phosphoric acid ($H_3PO_4$) is generally added to commercially available oxidizing agent solutions such as hydrogen peroxide as a stabilizer to inhibit the decomposition of the oxidizing agent. Several types of reagents, such as $H_3PO_3$, uric acid, $Na_2CO_3$, $KHCO_3$, barbituric acid, hippuric acid, urea, and acetanilide, have also been reported to serve as stabilizers for oxidizing agents such as hydrogen peroxide. These stabilizers have been shown to have a catalyst effect on some of the described reactions and an inhibitory effect on other areas of the reactions, but the reaction may proceed with or without stabilizers present in oxidizing agents, as desired.

Various embodiments of the present disclosure have applications in many industries. By increasing the efficacy of oxidizing agents, common chemical reactions involving oxidizing agents are accomplished using less volume and/or a lower concentration of oxidizing agents. According to various embodiments, oxidizing agents are used to precipitate material out of solution. Increasing the efficacy of the oxidizing agent allows for this precipitation with less oxidizing agent.

Oxidizing agents have antimicrobial properties. According to various embodiments, by increasing the antimicrobial efficacy with the methods described herein, concentrations of oxidizing agents utilized are reduced while efficacy is maintained or increased. By utilizing various embodiments in a small micron antimicrobial dry fog photon/phonon enhanced oxidizing agent solution, an extremely low concentration of a photon enhanced hydrogen peroxide solution (with wavelengths that dissociate trioxygen excluded) is deposited in ambient air through a HVAC system rendering the air almost microbe free in a matter of a few hours. According to various embodiments, by increasing the availability of ROS in the photon emission enhanced oxidizing agent solution, applications of oxidizing agents in the semiconductor industry, paper industry, petrochemical industry, and other commercial applications are accomplished faster, more economically, and/or more environmentally responsibly. The uses of the embodiments described herein are numerous and widespread in diverse industries from oil and gas to health care and beyond.

The foregoing description and accompanying figures illustrate the principles, embodiments, and modes of operation of the present disclosure. However, the disclosure should not be construed as being limited to the embodiments discussed herein. Additional variations of the embodiments will be appreciated by those skilled in the art. Therefore, the various embodiments should be regarded as illustrative rather than restrictive. Accordingly, it should be appreciated that variations to the embodiments described herein can be made by those skilled in the art without departing from the scope of the disclosure as defined by the following claims.

According to various embodiments of the present disclosure, a method for enhancing the effectiveness of products generated from photo-oxidation reactions, photocatalytic reactions, and/or photochemical combined with photocatalytic reactions is provided. The reaction contains one or more of, hydrogen and/or its isotopes, oxygen and/or its isotopes, electronically modified oxygen derivatives, reactive oxygen species, trioxygen, hydrons, hydroperoxyls, and other free radicals. Various embodiments of the method include: applying at least one oxidizing agent to a target or a substance to be treated; applying photon and/or phonon emissions at one or more wavelength in a range from 0.001 nm to 845 nm (where 0.01 nm is the lower limit of ionizing x-ray photons and 845 nm is the upper limit of photons that will dissociate water) to the oxidizing agent, the target, and/or the substance to be treated, wherein wavelengths that photo-dissociate trioxygen are excluded; and performing an oxidizing reaction between the at least one oxidizing agent and the target and/or substance to be treated, which produces the photo-oxidation reaction products, photocatalytic reaction products, and/or photochemical combined with photocatalytic reaction products, wherein the photo oxidation reaction products, photocatalytic reaction products, and/or photochemical combined with photocatalytic reaction products generate at least one of trioxygen, hydrogen and its ions, oxygen and its ions, hydroxyl radical, hydrons, hydroperoxyls, and electronically modified oxygen derivatives.

In various embodiments of the method, the excluded wavelengths are one or more of 197 nm-198 nm, 263 nm-264 nm, 307 nm-308 nm, 402 nm-403 nm, 452 nm-453 nm, 599 nm-600 nm, and 1118 nm-1119 nm.

In various embodiments of the method, the photon and/or phonon emissions are applied by an emission source selected from an electromagnetic radiation emitting bulb, a light emitting diode, or a laser.

In various embodiments of the method, the photon and/or phonon emissions are applied directly or indirectly to the oxidizing agent, the target, and/or the substance to be treated.

In various embodiments of the method, the at least one oxidizing agent is applied to the target or the substance to be treated with an oxidizing agent dispenser selected from a pump, mister, fogger, atomizer, diffuser, electrostatic sprayer, or other suitable device that dispenses the oxidizing agent in a desired particle size.

Various embodiments of the method further include applying additional reactants at various stages to aid the oxidizing reaction, wherein the additional reactants are selected from enzymes, catalysts, stabilizers, and flocculants.

In various embodiments of the method, the product is used to precipitate and/or agglomerate material out of a liquid, plasma, air, or gas. In various embodiments of the method, the product is an antimicrobial agent. In various embodiments of the method, the product is a bleaching agent. In various embodiments of the method, the product is a catalyst, reactant, or other substance providing hydroxyl radicals or other reactive oxygen species.

In various embodiments of the method, the photon and/or phonon emissions are applied as a single wavelength or multiple wavelengths, applied either independently or simultaneously, and applied either continuously or pulsed. In various embodiments of the method, the photon emissions are applied to the oxidizing agent, the target, and/or the substance to be treated at a dose that is varied or not varied.

In various embodiments of the method, the amount of the at least one oxidizing agent is in a range from 1 part per million to 50 percent of the volume of the target and/or substance to be treated.

In various embodiments of the method, the photon emissions are applied to the at least one oxidizing agent before the at least one oxidizing agent is applied to the target and/or the substance to be treated, the target and/or the substance to be treated furthers the oxidization reaction or produces one or more additional reaction, and the further or one or more additional reactions are not dependent on continued or additional application of the photon emissions.

In various embodiments of the method, the photon emissions are applied to the at least one oxidizing agent after the at least one oxidizing agent is applied to the target and/or substance to be treated so that trioxygen and other reaction products are generated after the at least one oxidizing agent is applied to the target and/or substance to be treated, and the oxidization reaction is readied but not initiated until a preset time or event.

In various embodiments of the method, the oxidation reaction occurs in a sealed container whereby gases created by the oxidation reaction are not allowed to escape.

In various embodiments of the method, the at least one oxidizing agent is selected from oxygen ($O_2$), trioxygen ($O_3$), hydrogen (H), hydrogen peroxide ($H_2O_2$), inorganic peroxides, Fenton's reagent, fluorine ($F_2$), chlorine ($Cl_2$), halogens, nitric acid ($HNO_3$), nitrate compounds, sulfuric acid ($H_2SO_4$), peroxydisulfuric acid ($H_2S2O_8$), peroxymonosulfuric acid ($H_2SO_5$), sulfur compounds, hypochlorite, chlorite, chlorate, perchlorate, other analogous halogen compounds, chromic acid, dichromic acid, calcium oxide, chromium trioxide, pyridinium chlorochromate (PCC), chromate, dichromate compounds, hexavalent chromium compounds, potassium permanganate ($KMnO_4$), sodium perborate, permanganate compounds, nitrous oxide (N20), nitrogen dioxide/dinitrogen tetroxide ($NO_2$/N204), urea, potassium nitrate ($KNO_3$), sodium bismuthate ($NaBiO_3$), ceric ammonium nitrate, ceric sulfate, cerium (IV) compounds, peracetic acid, and lead dioxide ($PbO_2$).

Various embodiments of the method further include determining the formulation of the at least one oxidizing agent, wherein the formulation is based on one or more properties of whether the target and/or substance to be treated is under aerobic or anaerobic conditions, pH of the target and/or substance to be treated, temperature of the target and/or substance to be treated, salinity of the target and/or substance to be treated, consortium or population characteristics of organisms or micro-organism present, content of the target and/or substance to be treated, or content of any biofilms associated with the target and/or substance to be treated.

In various embodiments of the method, the at least one oxidizing agent further includes at least one other substance that aids in a desired process when applied to the target and/or substance to be treated, the desired process selected from antimicrobial properties, anti-corrosion properties, anti-neoplastic properties, thermal properties, explosive properties, precipitation properties, electrochemical properties, and power generation properties.

In various embodiments of the method, at least one of the photon emission wavelengths, intensity, duration, or location relative to the target and/or substance to be treated is determined on the basis of any one or more of: the density and light absorbing or reflection quality of the target and/or substance to be treated; the size, shape, or composition of a container containing the target and/or substance to be treated; conditions or properties of the environment of the target and/or substance to be treated; whether the target and/or substance to be treated is under aerobic or anaerobic conditions; pH, temperature, salinity of the target and/or substance to be treated; consortium or population characteristics of any organisms or microorganisms present in the target and/or substance to be treated; microbial content of the target and/or substance to be treated; and microbial content of any biofilm present in the target and/or substance to be treated; or a container containing the target and/or substance to be treated.

In various embodiments of the method, the concentration, temperature, viscosity, and/or pH of the at least one oxidizing agent is adjusted to produce a desired reaction or results.

In various embodiments of the method, the at least one oxidizing agent, target and/or substance to be treated is a liquid, solid, gas, plasma, or combination thereof, either independently or simultaneously.

In various embodiments of the method, the oxidation reaction is affected or initiated by an addition of other catalysts.

In various embodiments of the method, the duration of the photon emissions is in a range from 1 second to 30 minutes, the emissions continuous, pulsed, or intermittent.

In various embodiments of the method, the at least one oxidizing agent, target, and/or substance to be treated is heated or cooled to activate and/or inactivate enzymes present in the target and/or substance to be treated.

In various embodiments of the method, the pH of the oxidizing agent, target, and/or substance to be treated is optimized to aid in the formation of a desired reactive oxygen species, and/or wherein the pH of the oxidizing agent, target, and/or substance to be treated is optimized to aid in elimination or reduction in activity of selected reactive oxygen species.

According to various embodiments of the present disclosure, a system is configured to perform a method for enhancing the effectiveness of products generated from photo-oxidation reactions, photocatalytic reactions, photochemical reactions, and/or photochemical combined with photocatalytic reactions. The system includes: a reaction area, in which the at least one oxidizing agent functions together with photon and/or phonon emissions to perform the oxidation reaction, so that products of the oxidation reaction can be collected and separated at any time during the reaction; at least one oxidizing agent introducing component for applying the at least one oxidizing agent to the target and/or substance to be treated; and at least one photon emitting component for creating the photon emissions.

Various embodiments of the system further include one or more sensors or other devices to indicate, detect, or inform of one or more of the following properties of the target or storage or environment: pH, temperature, salinity, density, trioxygen concentration, oxygen concentration, hydrogen concentration, oxidizing agent concentration, flow rate, microbial content, presence or absence of bacterial species, presence or absence of corrosive metabolites or otherwise corrosive substance, identification of a gas, presence or absence of an aqueous environment, presence or absence of high, low, or otherwise concentration of bacteria or non-bacteria, biomass or non-biomass, or microbial content, and location of biofilms.

In various embodiments of the system, the at least one photon emitting component emits, delivers, produces, or otherwise facilitates photon emissions in a range from 0.01 nanometers to 845 nanometers, independently, simultaneous, continuously, or intermittently, and the at least one photon emitting component is suspended, adjacent to, inside of, surrounding, or associated with a container, structure, area of the at least one oxidizing agent, the target, and/or substance to be treated, and/or supported in a target container, and wherein the at least one photon emitting component is or is not physically close to the at least one oxidizing agent, the target, and/or the substance to be treated.

In various embodiments of the system, the at least one photon emitting component adjusts one or more of the photon emission wavelengths, intensity, duration, or location relative to the target and/or substance to be treated on the basis of any one or more of the density and light absorbing or reflection quality of the target and/or substance to be treated, the size, shape, or composition of the reaction area, conditions or properties of the environment, whether the target and/or substance to be treated is under aerobic or anaerobic conditions, pH, temperature, or salinity of the target and/or substance to be treated, consortium or population characteristics of any organisms or micro-organisms present in the target and/or substance to be treated, microbial content of the target and/or substance to be treated, and the microbial content of any biofilm present in the target and/or substance to be treated, the reaction area, or the environment where the system of this disclosure is to take place.

What is claimed is:

1. A method for enhancing effectiveness of products generated from photo-oxidation reactions, photocatalytic reactions, photochemical reactions, and/or photochemical combined with photocatalytic reactions, the reactions comprising one or more of reactive, hydrogen and/or its isotopes, oxygen and/or its isotopes, electronically modified oxygen derivatives, reactive oxygen species, trioxygen, hydrons, hydroperoxyls, and other free radicals, the method comprising:

applying at least one oxidizing agent to a target or a substance to be treated;

applying photon emissions at one or more wavelength in a range from 0.01 nm to 845 nm to the at least one oxidizing agent, the target, and/or the substance to be treated, wherein wavelengths that photo-dissociate trioxygen are excluded, and the excluded wavelengths comprise 263 nm-264 nm;

performing an oxidizing reaction between the at least one photon enhanced oxidizing agent and the target and/or substance to be treated, which produces the photo-oxidation reaction products, photocatalytic reaction products, photochemical reaction products, and/or photochemical combined with photocatalytic reaction products, wherein the photo oxidation reaction products, photocatalytic reaction products, photochemical reaction products, and/or photochemical combined with photocatalytic reaction products generate at least one of trioxygen, hydrogen and its ions, oxygen and its ions, hydroxyl radical, hydrons, hydroperoxyls, trioxidane, and electronically modified oxygen derivatives;

wherein concentration, temperature, viscosity, and/or pH of the at least one oxidizing agent are adjusted to produce a desired reaction or results.

2. The method of claim 1, wherein the excluded wavelengths are further selected from the group consisting of 197 nm-198 nm, 307 nm-308 nm, 402 nm-403 nm, 452 nm-453 nm, 599 nm-600 nm, and 1118 nm-1119 nm.

3. The method of claim 1, wherein the photon emissions are applied by an emission source selected from the group consisting of an electromagnetic radiation emitting bulb, Light Emitting Diode, x-ray generator, and laser.

4. The method of claim 1, wherein photon emissions are applied directly or indirectly to the oxidizing agent, the target, and/or the substance to be treated.

5. The method of claim 1, wherein the at least one oxidizing agent is applied to the target or the substance to be treated with an oxidizing agent dispenser selected from the group consisting of a pump, mister, fogger, atomizer, diffuser, electrostatic sprayer, or other suitable device that dispenses the oxidizing agent in a desired particle size.

6. The method of claim 1, further comprising applying additional reactants at various stages to aid the oxidizing reaction, wherein the additional reactants are selected from the group consisting of enzymes, catalysts, stabilizers, and flocculants.

7. The method of claim 1, wherein the photon enhanced oxidizing agent is used to precipitate and/or agglomerate material out of a liquid, plasma, air, or gas.

8. The method of claim 1, wherein the photon enhanced oxidizing agent is an antimicrobial agent.

9. The method of claim 1, wherein the photon enhanced oxidizing agent is a bleaching agent.

10. The method of claim 1, wherein the photon enhanced oxidizing agent is a catalyst, reactant, or other substance providing hydroxyl radicals or other reactive oxygen species.

11. The method of claim 1, wherein the photon emissions are applied as a single wavelength or multiple wavelengths, applied either independently or simultaneously, and either continuously or pulsed.

12. The method of claim 1, wherein the photon emissions are applied to the oxidizing agent, the target, and/or the substance to be treated at a dose that is varied or not varied.

13. The method of claim 1, wherein the amount of the at least one oxidizing agent is in a range from 1 part per million to 50 percent of the volume of the target and/or substance to be treated.

14. The method of claim 1, wherein the photon emission is applied to the at least one oxidizing agent before the at least one oxidizing agent is applied to the target and/or the substance to be treated, the target and/or the substance to be treated furthers the oxidization reaction or produces one or more additional reaction, and the further oxidization reaction or one or more additional reactions are not dependent on continued or additional application of the photon and/or phonon emissions.

15. The method of claim 1, wherein the photon emission is applied to the at least one oxidizing agent after the at least one oxidizing agent is applied to the target and/or substance to be treated so that trioxygen and other reaction products are generated after the at least one oxidizing agent is applied to the target and/or substance to be treated, and the oxidization reaction is readied but not initiated until a preset time or event.

16. The method of claim 1, wherein the oxidation reaction utilizing the photon enhanced oxidizing agent occurs in a sealed container whereby gases created by the oxidation reaction are not allowed to escape.

17. The method of claim 1, wherein the at least one oxidizing agent is selected from the group consisting of oxygen ($O_2$), trioxygen ($O_3$), hydrogen (H), hydrogen peroxide ($H_2O_2$), inorganic peroxides, Fenton's reagent, fluorine ($F_2$), chlorine ($Cl_2$), halogens, nitric acid ($HNO_3$), nitrate compounds, sulfuric acid ($H_2SO_4$), peroxydisulfuric acid ($H_2S_2O_8$), peroxymonosulfuric acid ($H_2SO_5$), sulfur compounds, hypochlorite, chlorite, chlorate, perchlorate, other analogous halogen compounds, chromic acid, dichromic acid, calcium oxide, chromium trioxide, pyridinium chlorochromate (PCC), chromate, dichromate compounds, hexavalent chromium compounds, potassium permanganate ($KMnO_4$), sodium perborate, permanganate compounds, nitrous oxide ($N_2O$), nitrogen dioxide/dinitrogen tetroxide ($NO_2/N_2O_4$), urea, potassium nitrate ($KNO_3$), sodium bismuthate ($NaBiO_3$), ceric ammonium nitrate, ceric sulfate, cerium (IV) compounds, peracetic acid, and lead dioxide ($PbO_2$).

18. The method of claim 1, further comprising determining the formulation of the at least one oxidizing agent, wherein the formulation is based on one or more properties of whether the target and/or substance to be treated is under aerobic or anaerobic conditions, pH of the target and/or substance to be treated, temperature of the target and/or substance to be treated, salinity of the target and/or substance to be treated, consortium or population characteristics of organisms or micro-organism present, content of the target and/or substance to be treated, or content of any biofilms associated with the target and/or substance to be treated.

19. The method of claim 1, wherein the at least one photon enhanced oxidizing agent further comprises at least one other substance that aids in a desired process when applied to the target and/or substance to be treated, the desired process selected from the group consisting of antimicrobial properties, anti-corrosion properties, anti-neoplastic properties, thermal properties, explosive properties, precipitation properties, electrochemical properties, and power generation properties.

20. The method of claim 1, wherein at least one of the photon emission wavelengths, intensity, duration, or location relative to the target and/or substance to be treated is determined on the basis of any one or more of: the density and light absorbing or reflection quality of the target and/or substance to be treated; the size, shape, or composition of a container containing the target and/or substance to be treated; conditions or properties of the environment of the target and/or substance to be treated; whether the target and/or substance to be treated is under aerobic or anaerobic conditions; pH, temperature, salinity of the target and/or substance to be treated; consortium or population characteristics of any organisms or microorganisms present in the target and/or substance to be treated; microbial content of the target and/or substance to be treated; and microbial content of any biofilm present in the target and/or substance to be treated; or a container containing the target and/or substance to be treated.

21. The method of claim 1, wherein the at least one oxidizing agent and the target and or substance to be treated is a liquid, solid, gas, plasma, or combination thereof, either independently or simultaneously.

22. The method of claim 1, wherein the oxidation reaction is affected or initiated by the addition of other catalysts.

23. The method of claim 1, wherein the duration of the photon emissions is in a range from 1 second to 30 minutes, the emissions continuous, pulsed, or intermittent.

24. The method of claim 1, wherein the at least one oxidizing agent, target, and/or substance to be treated is heated or cooled to activate and/or inactivate enzymes present in the target and/or substance to be treated.

25. The method of claim 1, wherein the pH of the oxidizing agent, target, and/or substance to be treated is optimized to aid in the formation of a desired reactive oxygen species and/or wherein the pH of the oxidizing agent, target and/or substance to be treated is optimized to aid in elimination or reduction in activity of selected reactive oxygen species.

* * * * *